US007166692B2

(12) United States Patent
Karas

(10) Patent No.: US 7,166,692 B2
(45) Date of Patent: Jan. 23, 2007

(54) INTRACELLULAR DELIVERY OF SMALL MOLECULES, PROTEINS, AND NUCLEIC ACIDS

(75) Inventor: Michael Karas, Rockville, MD (US)

(73) Assignee: Canbrex Bio Science Walkersville, Inc., Walkersville, MD (US)

( * ) Notice: Subject to any disclaimer, the term of this patent is extended or adjusted under 35 U.S.C. 154(b) by 169 days.

(21) Appl. No.: 10/790,768

(22) Filed: Mar. 3, 2004

(65) Prior Publication Data

US 2004/0209797 A1    Oct. 21, 2004

Related U.S. Application Data

(60) Provisional application No. 60/451,243, filed on Mar. 4, 2003.

(51) Int. Cl.
*C07K 7/00* (2006.01)

(52) U.S. Cl. .................... 530/300; 514/2; 424/1.11

(58) Field of Classification Search .............. None
See application file for complete search history.

(56) References Cited

U.S. PATENT DOCUMENTS

| 5,652,122 | A | 7/1997 | Frankel et al. |
| 5,670,617 | A | 9/1997 | Frankel et al. |
| 5,674,980 | A | 10/1997 | Frankel et al. |
| 5,747,641 | A | 5/1998 | Frankel et al. |
| 5,804,604 | A | 9/1998 | Frankel et al. |
| 5,807,746 | A | 9/1998 | Lin et al. |
| 6,093,809 | A | 7/2000 | Cech et al. |
| 6,166,178 | A | 12/2000 | Cech et al. |
| 6,261,836 | B1 | 7/2001 | Cech et al. |
| 6,306,993 | B1 | 10/2001 | Rothbard et al. |
| 6,358,739 | B1 | 3/2002 | Baetge et al. |
| 2002/0009491 | A1 | 1/2002 | Rothbard et al. |

FOREIGN PATENT DOCUMENTS

| EP | 0 841 396 A1 | 5/1996 |
| WO | WO - 99/50386 | 10/1999 |
| WO | WO - 00/34308 | 6/2000 |
| WO | WO - 00/61617 | 10/2000 |
| WO | WO - 00/62067 | 10/2000 |
| WO | WO - 01/15511 | 3/2001 |

OTHER PUBLICATIONS

Falnes et al. Biochemistry 40: 4349-4358 (2001). "Ability of the Tat Basic Domain and VP22 to mediate cell binding, but not membrane translocation of the Diptheria Toxin A-fragment".*
Violini et al. Biochemistry 41: 12652-12661 (2002). "Evidence for a plasma membrane-mediated permeability barrier to Tat Basic Domain in well-differentiated epithelial cells: lack of correlation with heparan sulfate".*
Wadia and Dowdy, "Protein transduction technology", Current Opinion in Biotechnology 13: 52-56 (2002).*
Schwarze et al., "Protein transduction: unrestricted delivery into all cells?", Trends in Cell Biology 10: 290-295 (2000).*
Wender, et al., "The design, synthesis, and evaluation of melecules that enable or enhance cellular uptake: Peptoid molecular transmporters" PNAS, vol. 97, No. 24, Nov. 21, 2000, pp. 13003-13008.
Walther, et al., "Expression of Granulosa Cell-Specific Genes and Induction of Apoptosis in Conditionally Immortalized Granulosa Cell Lines Established from H-2K[b]-tsA58 Transgenic Mice" Biology of Reproduction, vol. 60, 1999, pp. 1078-1086.
Ho, et al., "Synthetic Protein Transduction Domains: Enhanced Transduction Potential in Vitro and in Vivo[1]" Cancer Research, vol. 61, Jan. 15, 2001, pp. 474-477.
Asoh, et al., "Protection against ischemic brain injury by protein therapeutics" PNAS, vol. 99, No. 26, Dec. 24, 2002, pp. 17107-17112.
Cao, et al., "In Vivo Delivery of a Bcl-xL Fusion Protein Containing the TAT Protein Transduction Domain Protects against Ischemic Brain Injury and Neuronal Apoptosis" Jorunal of Neuroscience, vol. 22, No. 13, Jul. 1, 2002, pp. 5423-5431.
Pierce Chemical Technical Library, "Cross—Linking: Homobifunctional Cross-linkers" http://www.piercenet.com, (2002).
Pierce Chemical Technical Library, "Cross—Linking: Heterobifunctional Cross-linkers" http://www.piercenet.com, (2002).
Pierce Chemical Technical Library, "Cross—Linking: Applications for Use of Cross-linkers" http://www.piercenet.com, (2002).
Pierce Chemical Technical Library, "Cross—Linking: Glossary of Cross-linking Terms" http://www.piercenet.com, (2002).
Conejero et al., "Glutamate and Antimitotic Agents Induce Differentiation, p53 Activation, and Apoptosis in Rodent Neostriatal Cell Lines Immortalized with the tsA58 Allele of SV40 Large T Antigen," 1999, *Experimental Neurology*, vol. 158, pp. 109-120.
Derer et al., "Direct Protein Transfer to Terminally Differentiated Muscle Cells," 1999, *J. Mol. Med.*, vol. 77, pp. 609-613, Examiner Placing in File.
Guenal et al., "Bcl-2 and Hsp27 Act at Different Levels to Suppress Programmed Cell Death," 1997, *Oncogene*, vol. 15, pp. 347-360.
Kim et al., "Survival of Conditionally Immortalized Hepatocytes in the Spleen of Syngeneic Rats," 2001, *Journal of Gastroenterology and Hepatology*, vol. 16, pp. 52-60.
Mi et al., "Characterization of a Class of Cationic Peptides Able to Facilitate Efficient Protein Transduction in Vitro and in Vivo," Oct. 2000, *Molecular Therapy*, vol. 2, No. 4, pp. 339-347.

(Continued)

*Primary Examiner*—Jon Weber
*Assistant Examiner*—Anand Desai
(74) *Attorney, Agent, or Firm*—Banner & Witcoff

(57) ABSTRACT

An amino acid sequence Arg-Lys-Met-Leu-Lys-Ser-Thr-Arg-Arg-Gln-Arg-Arg (SEQ ID NO:1) functions as a protein transduction domain (PTD) and is capable of delivering small molecules, proteins, and nucleic acids to an intracellular compartment of a cell. An amino terminal lysine linker improves the efficiency of the PTD. A nuclear localization signal can be used to target the PTD to a cell's nucleus. The PTD can be used in PTD-cargo moiety complexes that can reversibly immortalize cells and increase cell viability in culture.

15 Claims, 16 Drawing Sheets

OTHER PUBLICATIONS

Morris et al., "A Peptide Carrier for the Delivery of Biologically Active Proteins into Mammalian Cells," Dec. 2001, *Nature Biotechnology*, vol. 19, pp. 1173-1176.

Schwartz & Zhang, "Peptide-Mediated Cellular Delivery," 2000, *Current Opinion in Molecular Therapeutics*, vol. 2(2) (5 pages).

Urquidi et al., "Role of Telomerase in Cell Senescence and Oncogenesis," 2000, *Ann. Rev. Med.*, vol. 51, pp. 65-79.

Vocero-Akbani et al., "Protein Transduction: Delivery of Tat-GTPase Fusion Proteins into Mammalian Cells," *Regulators and Effectors of Small GTPases*, vol. 332, pp. 36-49, 2001.

Wadia & Dowdy, "Protein Transduction Technology," 2002, *Curr. Opin. Biotechnology*, vol. 13, pp. 52-56.

Dietz et al., "Inhibition of Neuronal Apoptosis *in Vitro* and *in Vivo* Using TAT-Mediated Protein Transduction", *Molecular and Cellular Neuroscience*, 2002, pp. 29-37, vol. 21.

Fawall et al., "Tat-mediated delivery of heterologous proteins into cells", Biogen Inc., Oct. 7, 1993, pp. 664-668.

Elliott and O'Hare, "Intercellular Trafficking and Protein Delivery by a Herpsvirus Structural Protein" (1997) *Cell* 88:223-233.

\* cited by examiner

SEQUENCE LISTING

```
<160> NUMBER OF SEQ ID NOS: 25

<210> SEQ ID NO 1
<211> LENGTH: 12
<212> TYPE: PRT
<213> ORGANISM: Artificial Sequence
<220> FEATURE:
<223> OTHER INFORMATION: protein transduction domain

<400> SEQUENCE: 1

Arg Lys Met Leu Lys Ser Thr Arg Arg Gln Arg Arg
1               5                   10

<210> SEQ ID NO 2
<211> LENGTH: 15
<212> TYPE: PRT
<213> ORGANISM: Artificial Sequence
<220> FEATURE:
<223> OTHER INFORMATION: protein transduction domain

<400> SEQUENCE: 2

Lys Gly Gly Arg Lys Met Leu Lys Ser Thr Arg Arg Gln Arg Arg
1               5                   10                  15

<210> SEQ ID NO 3
<211> LENGTH: 6
<212> TYPE: PRT
<213> ORGANISM: Artificial Sequence
<220> FEATURE:
<223> OTHER INFORMATION: nuclear localization signal

<400> SEQUENCE: 3

Lys Lys Lys Arg Lys Val
1               5

<210> SEQ ID NO 4
<211> LENGTH: 21
<212> TYPE: PRT
<213> ORGANISM: Artificial Sequence
<220> FEATURE:
<223> OTHER INFORMATION: protein transduction domain

<400> SEQUENCE: 4

Lys Gly Gly Arg Lys Met Leu Lys Ser Thr Arg Arg Gln Arg Arg Lys
1               5                   10                  15
```

```
Lys Lys Arg Lys Val
            20

<210> SEQ ID NO 5
<211> LENGTH: 27
<212> TYPE: PRT
<213> ORGANISM: Artificial Sequence
<220> FEATURE:
<223> OTHER INFORMATION: protein transduction domain

<400> SEQUENCE: 5

Lys Gly Gly Lys Lys Arg Lys Val Arg Met Leu Lys Ser Thr
1               5                   10                  15

Arg Arg Gln Arg Arg Lys Lys Arg Lys Val
            20                  25

<210> SEQ ID NO 6
<211> LENGTH: 14
<212> TYPE: PRT
<213> ORGANISM: Artificial Sequence
<220> FEATURE:
<223> OTHER INFORMATION: negative control peptide
<220> FEATURE:
<221> NAME/KEY: MISC_FEATURE
<222> LOCATION: (1)..(1)
<223> OTHER INFORMATION: Biotin

<400> SEQUENCE: 6

Gly Gly Ala Arg Pro Leu Glu His Gly Ser Asp Lys Ala Thr
1               5                   10

<210> SEQ ID NO 7
<211> LENGTH: 14
<212> TYPE: PRT
<213> ORGANISM: Artificial Sequence
<220> FEATURE:
<223> OTHER INFORMATION: protein transduction domain
<220> FEATURE:
<221> NAME/KEY: MISC_FEATURE
<222> LOCATION: (1)..(1)
<223> OTHER INFORMATION: Biotin

<400> SEQUENCE: 7

Gly Gly Gly Tyr Gly Arg Lys Lys Arg Arg Gln Arg Arg Arg
1               5                   10

<210> SEQ ID NO 8
<211> LENGTH: 14
<212> TYPE: PRT
<213> ORGANISM: Artificial Sequence
<220> FEATURE:
<223> OTHER INFORMATION: protein transduction domain
<220> FEATURE:
<221> NAME/KEY: MISC_FEATURE
<222> LOCATION: (14)..(14)
<223> OTHER INFORMATION: Biotin

<400> SEQUENCE: 8

Tyr Gly Arg Lys Lys Arg Arg Gln Arg Arg Arg Gly Gly Lys
1               5                   10

<210> SEQ ID NO 9
<211> LENGTH: 14
<212> TYPE: PRT
<213> ORGANISM: Artificial Sequence
<220> FEATURE:
<223> OTHER INFORMATION: protein transduction domain
<220> FEATURE:
```

```
<221> NAME/KEY: MISC_FEATURE
<222> LOCATION: (1)..(1)
<223> OTHER INFORMATION: Biotin

<400> SEQUENCE: 9

Gly Gly Gly Tyr Ala Arg Ala Ala Ala Arg Gln Ala Arg Ala
1               5                   10

<210> SEQ ID NO 10
<211> LENGTH: 14
<212> TYPE: PRT
<213> ORGANISM: Artificial Sequence
<220> FEATURE:
<223> OTHER INFORMATION: protein transduction domain
<220> FEATURE:
<221> NAME/KEY: MISC_FEATURE
<222> LOCATION: (14)..(14)
<223> OTHER INFORMATION: Biotin

<400> SEQUENCE: 10

Tyr Ala Arg Ala Ala Ala Arg Gln Ala Arg Ala Gly Gly Lys
1               5                   10

<210> SEQ ID NO 11
<211> LENGTH: 15
<212> TYPE: PRT
<213> ORGANISM: Artificial Sequence
<220> FEATURE:
<223> OTHER INFORMATION: protein transduction domain
<220> FEATURE:
<221> NAME/KEY: MISC_FEATURE
<222> LOCATION: (15)..(15)
<223> OTHER INFORMATION: Biotin

<400> SEQUENCE: 11

Arg Arg Gln Arg Arg Thr Ser Lys Leu Met Lys Arg Gly Gly Lys
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: protein transduction domain
<220> FEATURE:
<221> NAME/KEY: MISC_FEATURE
<222> LOCATION: (1)..(1)
<223> OTHER INFORMATION: Biotin

<400> SEQUENCE: 12

Gly Gly Gly Arg Arg Gln Arg Arg Thr Ser Lys Leu Met Lys Arg
1               5                   10                  15

<210> SEQ ID NO 13
<211> LENGTH: 14
<212> TYPE: PRT
<213> ORGANISM: Artificial Sequence
<220> FEATURE:
<223> OTHER INFORMATION: protein transduction domain
<220> FEATURE:
<221> NAME/KEY: MISC_FEATURE
<222> LOCATION: (1)..(1)
<223> OTHER INFORMATION: Biotin

<400> SEQUENCE: 13

Lys Gly Gly Arg Arg Arg Gln Arg Arg Lys Lys Arg Gly Tyr
1               5                   10

<210> SEQ ID NO 14
```

```
<211> LENGTH: 15
<212> TYPE: PRT
<213> ORGANISM: Artificial Sequence
<220> FEATURE:
<223> OTHER INFORMATION: protein transduction domain
<220> FEATURE:
<221> NAME/KEY: MISC_FEATURE
<222> LOCATION: (1)..(1)
<223> OTHER INFORMATION: Biotin

<400> SEQUENCE: 14

Lys Gly Gly Arg Lys Met Leu Lys Ser Thr Arg Arg Gln Arg Arg
1               5                   10                  15

<210> SEQ ID NO 15
<211> LENGTH: 14
<212> TYPE: PRT
<213> ORGANISM: Artificial Sequence
<220> FEATURE:
<223> OTHER INFORMATION: protein transduction domain
<220> FEATURE:
<221> NAME/KEY: MISC_FEATURE
<222> LOCATION: (1)..(1)
<223> OTHER INFORMATION: Biotin

<400> SEQUENCE: 15

Gly Gly Gly Arg Arg Arg Gln Arg Arg Lys Lys Arg Gly Tyr
1               5                   10

<210> SEQ ID NO 16
<211> LENGTH: 15
<212> TYPE: PRT
<213> ORGANISM: Artificial Sequence
<220> FEATURE:
<223> OTHER INFORMATION: protein transduction domain
<220> FEATURE:
<221> NAME/KEY: MISC_FEATURE
<222> LOCATION: (1)..(1)
<223> OTHER INFORMATION: Biotin

<400> SEQUENCE: 16

Gly Gly Gly Arg Lys Met Leu Lys Ser Thr Arg Arg Gln Arg Arg
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: protein transduction domain
<220> FEATURE:
<221> NAME/KEY: MISC_FEATURE
<222> LOCATION: (1)..(1)
<223> OTHER INFORMATION: Biotin

<400> SEQUENCE: 17

Lys Gly Gly Arg Arg Gln Arg Arg Thr Ser Lys Leu Met Lys Arg
1               5                   10                  15

<210> SEQ ID NO 18
<211> LENGTH: 19
<212> TYPE: PRT
<213> ORGANISM: Artificial Sequence
<220> FEATURE:
<223> OTHER INFORMATION: protein transduction domain
<220> FEATURE:
<221> NAME/KEY: MISC_FEATURE
<222> LOCATION: (1)..(1)
<223> OTHER INFORMATION: Biotin

<400> SEQUENCE: 18
```

Lys Gly Gly Lys Lys Arg Lys Val Met Leu Lys Ser Thr Arg Arg
1               5                   10                  15

Gln Arg Arg

<210> SEQ ID NO 19
<211> LENGTH: 21
<212> TYPE: PRT
<213> ORGANISM: Artificial Sequence
<220> FEATURE:
<223> OTHER INFORMATION: protein transduction domain
<220> FEATURE:
<221> NAME/KEY: MISC_FEATURE
<222> LOCATION: (1)..(1)
<223> OTHER INFORMATION: Biotin

<400> SEQUENCE: 19

Lys Gly Gly Arg Lys Met Leu Lys Ser Thr Arg Arg Gln Arg Lys
1               5                   10                  15

Lys Lys Arg Lys Val
            20

<210> SEQ ID NO 20
<211> LENGTH: 21
<212> TYPE: PRT
<213> ORGANISM: Artificial Sequence
<220> FEATURE:
<223> OTHER INFORMATION: protein transduction domain
<220> FEATURE:
<221> NAME/KEY: MISC_FEATURE
<222> LOCATION: (1)..(1)
<223> OTHER INFORMATION: Biotin

<400> SEQUENCE: 20

Lys Lys Lys Arg Lys Val Lys Gly Gly Arg Lys Met Leu Lys Ser Thr
1               5                   10                  15

Arg Arg Gln Arg Arg
            20

<210> SEQ ID NO 21
<211> LENGTH: 25
<212> TYPE: PRT
<213> ORGANISM: Artificial Sequence
<220> FEATURE:
<223> OTHER INFORMATION: protein transduction domain
<220> FEATURE:
<221> NAME/KEY: MISC_FEATURE
<222> LOCATION: (1)..(1)
<223> OTHER INFORMATION: Biotin

<400> SEQUENCE: 21

Lys Gly Gly Lys Lys Arg Lys Val Met Leu Lys Ser Thr Arg Arg
1               5                   10                  15

Gln Arg Arg Lys Lys Lys Arg Lys Val
            20                  25

<210> SEQ ID NO 22
<211> LENGTH: 25
<212> TYPE: PRT
<213> ORGANISM: Artificial Sequence
<220> FEATURE:
<223> OTHER INFORMATION: protein transduction domain
<220> FEATURE:
<221> NAME/KEY: MISC_FEATURE
<222> LOCATION: (1)..(1)
<223> OTHER INFORMATION: Biotin

<400> SEQUENCE: 22

-continued

```
Lys Lys Lys Arg Lys Val Lys Gly Gly Lys Lys Arg Lys Val Met
1               5               10                  15

Leu Lys Ser Thr Arg Arg Gln Arg Arg
            20              25

<210> SEQ ID NO 23
<211> LENGTH: 11
<212> TYPE: PRT
<213> ORGANISM: Human immunodeficiency virus

<400> SEQUENCE: 23

Arg Arg Arg Gln Arg Arg Lys Lys Arg Gly Tyr
1               5                   10

<210> SEQ ID NO 24
<211> LENGTH: 11
<212> TYPE: PRT
<213> ORGANISM: Human immunodeficiency virus

<400> SEQUENCE: 24

Tyr Gly Arg Lys Lys Arg Arg Gln Arg Arg
1               5                   10

<210> SEQ ID NO 25
<211> LENGTH: 12
<212> TYPE: PRT
<213> ORGANISM: Artificial Sequence
<220> FEATURE:
<223> OTHER INFORMATION: internalizing peptide

<400> SEQUENCE: 25

Arg Arg Gln Arg Arg Thr Ser Lys Leu Met Lys Arg
1               5                   10
```

INTRACELLULAR DELIVERY OF SMALL MOLECULES, PROTEINS, AND NUCLEIC ACIDS

This application claims the benefit of U.S. provisional application Ser. No. 60/451,243 filed Mar. 4, 2003, which is incorporated herein by reference in its entirety.

FIELD OF THE INVENTION

The invention relates to the field of peptides that facilitate transport of a cargo moiety across cellular membranes, "intracellular delivery." In particular, it is related to peptides that function as a protein transduction domain for intracellular delivery of small molecules, proteins, and nucleic acids.

BACKGROUND OF THE INVENTION

A cell membrane presents a formidable barrier between a cell cytoplasm and its external environment. Cells are generally impermeable to small molecules, proteins, and nucleic acids. Some small molecules can diffuse across the cell membrane, but the rate of diffusion often is too slow to be useful.

Reagents and methods exist to deliver small molecules, proteins, and nucleic acids to an intracellular compartment of a cell. Examples of such reagents and methods include lipids, calcium phosphate, DEAE dextran, electroporation, gene gun particle bombardment, recombinant viral infection, and direct microinjection. Most current reagents and methods are either toxic to cells or result in only a few cells receiving the small molecule, protein, or nucleic acid. In addition, current reagents and methods are not practical for in vivo delivery of small molecules, proteins, or nucleic acids to cells.

Some peptides have an ability to cross the cell membrane and enter a cell. These peptides, termed "protein transduction domains" (PTDs), can be linked to a cargo moiety and can transport the cargo moiety across the cell membrane and into the cell. Such transport is termed "peptide transport" because the peptides transport cargo moieties across the cell membrane and into the cell. Cargo moieties can be small molecules, proteins, or nucleic acids.

Peptide transport provides an alternative for delivery of small molecules, proteins, or nucleic acids across the cell membrane to an intracellular compartment of a cell. One well characterized protein transduction domain (PTD) is a tat-derived peptide. Frankel et al. (U.S. Pat. No. 5,804,604, U.S. Pat. No. 5,747,641, U.S. Pat. No. 5,674,980, U.S. Pat. No. 5,670,617, and U.S. Pat. No. 5,652,122) demonstrated transport of a cargo protein (β-galactosidase or horseradish peroxidase) into a cell by conjugating a peptide containing amino acids 49–57 of tat to the cargo protein.

Penetratin can transport hydrophilic macromolecules across the cell membrane (Derossi et al., *Trends Cell Biol.*, 8:84–87 (1998)). Penetratin is a 16 amino acid peptide which corresponds to amino acids 43–58 of the homeodomain of Antennapedia, a *Drosophila* transcription factor which is internalized by cells in culture. However, penetratin-mediated peptide transport of nucleic acids longer than 55 bases and proteins longer than 100 amino acids is inefficient.

VP22, a tegument protein from Herpes simplex virus type 1 (HSV-1), has the ability to transport proteins and nucleic acids across a cell membrane (Elliot et al., *Cell* 88:223–233, 1997). Residues 267–300 of VP22 are necessary but may not be sufficient for transport. Because the region responsible for transport function has not been identified, the entire VP22 protein is commonly used to transport cargo proteins and nucleic acids across the cell membrane (Schwarze et al., *Trends Pharmacol Sci*, 21:45–48, 2000).

There is a continuing need in the art for peptides that can efficiently transport cargo moieties across a cell membrane and into an intracellular compartment of a cell.

BRIEF SUMMARY OF THE INVENTION

One embodiment of the invention provides an isolated and purified polypeptide with a protein transduction domain (PTD). The PTD comprises Arg-Lys-Met-Leu-Lys-Ser-Thr-Arg-Arg-Gln-Arg-Arg (SEQ ID NO:1).

Another embodiment of the invention provides an isolated and purified polynucleotide encoding Arg-Lys-Met-Leu-Lys-Ser-Thr-Arg-Arg-Gln-Arg-Arg (SEQ ID NO:1).

Yet another embodiment of the invention provides a vector. The vector comprises a polynucleotide encoding Arg-Lys-Met-Leu-Lys-Ser-Thr-Arg-Arg-Gln-Arg-Arg (SEQ ID NO:1).

Still yet another embodiment of the invention provides a host cell. The host cell comprises a vector. The vector comprises a polynucleotide encoding Arg-Lys-Met-Leu-Lys-Ser-Thr-Arg-Arg-Gln-Arg-Arg (SEQ ID NO:1).

Another embodiment of the invention provides a complex comprising a polypeptide with a PTD linked to a cargo moiety. The PTD comprises Arg-Lys-Met-Leu-Lys-Ser-Thr-Arg-Arg-Gln-Arg-Arg (SEQ ID NO:1).

Still another embodiment of the invention provides a polynucleotide encoding a fusion protein. The fusion protein comprises Arg-Lys-Met-Leu-Lys-Ser-Thr-Arg-Arg-Gln-Arg-Arg (SEQ ID NO:1) linked to a polypeptide cargo moiety.

Yet another embodiment of the invention provides a vector. The vector comprises a polynucleotide encoding a fusion protein. The fusion protein comprises Arg-Lys-Met-Leu-Lys-Ser-Thr-Arg-Arg-Gln-Arg-Arg (SEQ ID NO:1) linked to a polypeptide cargo moiety.

Still yet another embodiment of the invention provides a host cell. The host cell comprises a vector. The vector comprises a polynucleotide encoding a fusion protein. The fusion protein comprises Arg-Lys-Met-Leu-Lys-Ser-Thr-Arg-Arg-Gln-Arg-Arg (SEQ ID NO:1) linked to a polypeptide cargo moiety.

Another embodiment of the invention provides a method of delivering a cargo moiety to an intracellular compartment of a cultured cell. A cell is contacted in vitro with a complex. The complex comprises a polypeptide with a PTD linked to a cargo moiety. The PTD comprises Arg-Lys-Met-Leu-Lys-Ser-Thr-Arg-Arg-Gln-Arg-Arg (SEQ ID NO:1). The cargo moiety is thereby delivered to an intracellular compartment of the cell.

Still another embodiment of the invention provides a method of reversibly immortalizing a cell in culture. A cell is contacted in vitro with a complex. The complex comprises a polypeptide with a PTD linked to a cargo moiety. The PTD comprises Arg-Lys-Met-Leu-Lys-Ser-Thr-Arg-Arg-Gln-Arg-Arg (SEQ ID NO:1). The cargo moiety is an immortalization protein. The cell is thereby reversibly immortalized.

Yet another embodiment of the invention provides a reversibly immortalized cell. The cell is reversibly immor talized by a method in which the cell is contacted in vitro with a complex. The complex comprises a polypeptide with a PTD linked to a cargo moiety. The PTD comprises Arg-Lys-Met-Leu-Lys-Ser-Thr-Arg-Arg-Gln-Arg-Arg (SEQ ID NO:1). The cargo moiety is an immortalization protein. The cell is thereby reversibly immortalized.

Still another embodiment of the invention provides a method of increasing viability of a cell in culture. A cell is contacted in vitro with a complex. The complex comprises a polypeptide with a PTD linked to a cargo moiety. The cargo moiety is an antiapoptotic protein.

The invention thus provides the art with reagents and methods for delivering cargo moieties to an intracellular compartment of a cell.

DETAILED DESCRIPTION OF THE INVENTION

Protein Transduction Domains

Figure 1:
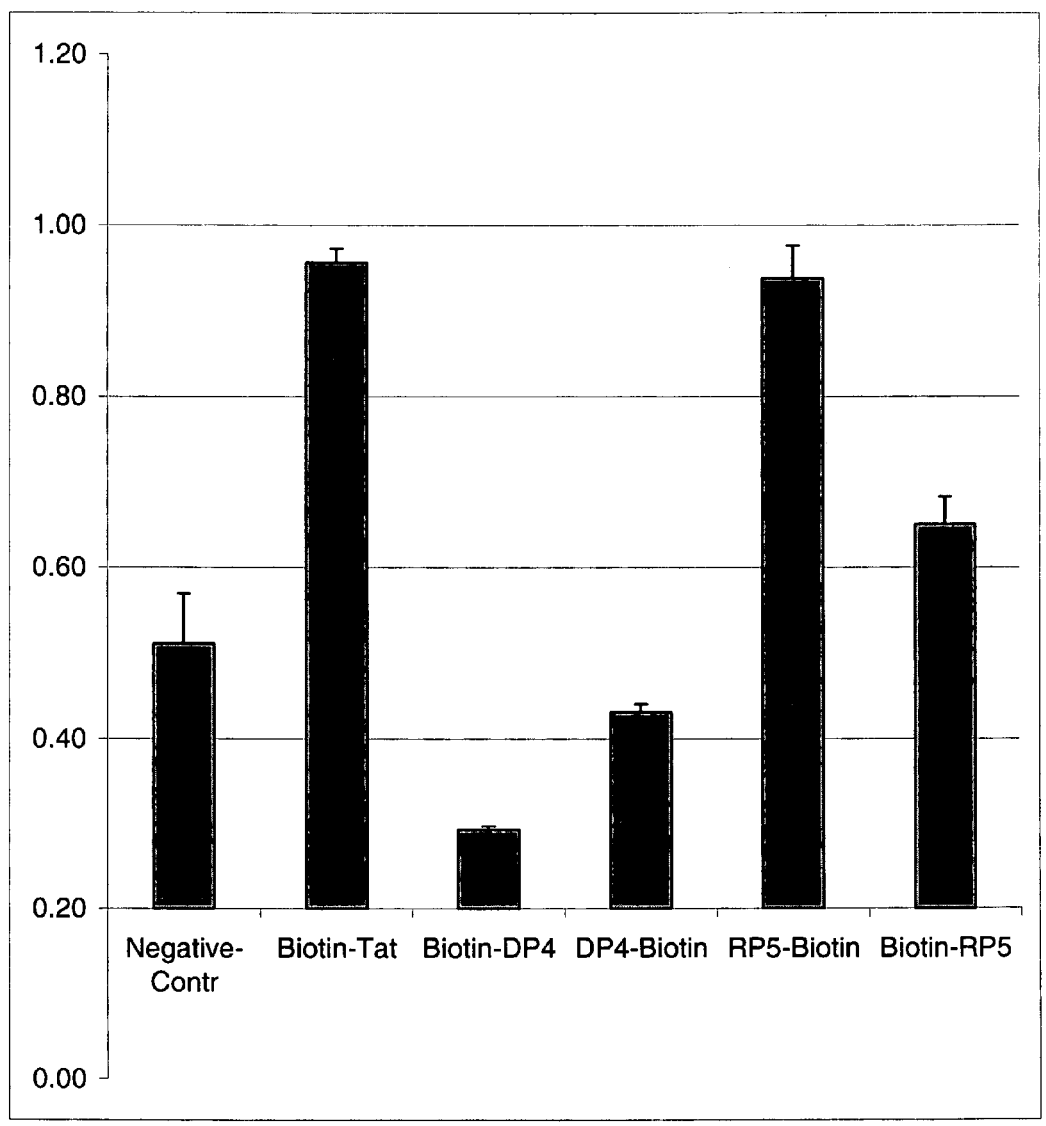
FIG. 1 shows the effect of different PTDs and biotin location on PTD-mediated transport of β-galactosidase.

Polypeptides with a protein transduction domain (PTD) having an amino acid sequence Arg-Lys-Met-Leu-Lys-Ser-Thr-Arg-Arg-Gln-Arg-Arg (SEQ ID NO:1) have the unexpected property of being able to cross a cell membrane and transport a cargo moiety to an intracellular compartment of a cell. SEQ ID NO: 1 is a reverse isomer of Arg-Arg-Gln-Arg-Arg-Thr-Ser-Lys-Met-Lys-Arg (SEQ ID NO:25), which was identified as an "internalizing peptide" in WO 01/15511.

Wender et al. (*Proc. Natl. Acad. Sci USA*, 97:13003–13008, 2000) reported that a reverse isomer of a tat-derived peptide (SEQ ID NO:23) (reverse tat) could cross the plasma membrane with an efficiency about three times that of a tat-derived peptide (SEQ ID NO:24) (tat). Wender et al. concluded that transport was not a function of chirality. The reason for the increase in transport efficiency with reverse tat (SEQ ID NO:23), however, was attributed to the arginine content at the amino terminus of the reverse tat peptide (SEQ ID NO:23). The first three amino acids in reverse tat (SEQ ID NO:23) are arginine, whereas tat (SEQ ID NO:24) contains only one arginine within the first three amino acids. In tat (SEQ ID NO:24), arginine content is highest at the carboxy terminus. The arginine content in SEQ ID NO:1 is highest within the carboxy terminus. Thus, the ability of the peptide of SEQ ID NO:1 to function as a PTD more efficiently than either tat (SEQ ID NO:24) or the WO 01/15511 peptide (SEQ ID NO:25) is unexpected.

Production of PTDs

PTDs of the present invention can be made by any method known in the art for synthesizing peptides. For example, PTDs can be synthesized chemically or can be made recombinantly.

Chemical Synthesis

PTDs can be synthesized in solid or solution phase, for example, using Fmoc or tBOC chemistries (Merrifield, *J. Am. Chem. Soc.* 85, 2149–2154, 1963; Roberge et al., *Science* 269, 202–204, 1995). Peptide synthesis can be performed using manual techniques or by automation. Automated synthesis can be achieved, for example, using an Applied Biosystems 431A Peptide Synthesizer (Perkin Elmer).

Recombinant Expression

Peptides can be made recombinantly by cloning a coding sequence for the peptide and expressing it in vitro. Any polynucleotide sequence that encodes a PTD can be used. The polynucleotide sequence can be synthesized in vitro using, e.g., phosphoroamidite chemistry. Nucleic acid synthesis can be performed using manual techniques or by automation. Automated synthesis can be achieved, for example, using an Applied Biosystems 3900 DNA Synthesizer (Perkin Elmer).

A PTD-encoding polynucleotide can be inserted into an expression vector which contains the necessary elements for the transcription and translation of the inserted coding sequence. Transcription and translation control elements include, for example, a promoter (e.g., T7 or T3), ribosome binding site, start codon, stop codon, and polyadenylation site. Methods which are well known to those skilled in the art can be used to construct expression vectors containing sequences encoding PTD-containing polypeptides and appropriate transcriptional and translational control elements. These methods include in vitro recombinant DNA techniques, synthetic techniques, and in vivo genetic recombination. Such techniques are described, for example, in Sambrook et al., 1989, MOLECULAR CLONING: A LABORATORY MANUAL (Cold Spring Harbor, N.Y.), and in Ausubel et al., CURRENT PROTOCOLS IN MOLECULAR BIOLOGY, John Wiley & Sons, New York, N.Y., 1989.

Expression in Host Cells

A variety of expression systems are available for expressing sequences that encode a PTD. Examples of such systems include, but are not limited to, bacteria, yeast, insect, plant, and animal cell systems. Bacteria can be transformed with recombinant bacteriophage, expression plasmids, or cosmid expression vectors. Yeast can be transformed with yeast expression vectors. Insect cells can be transfected with expression vectors or transduced with recombinant insect viruses (e.g., baculovirus). Plant cells can be transduced with recombinant plant viruses (e.g., cauliflower mosaic virus or tobacco mosaic virus). Animal cells can be transfected with expression vectors (e.g., pcDNA3 or pCMV-Sport) or transduced with recombinant viruses (e.g., retroviruses, adenoviruses, or semliki forest virus). Methods for transforming, transfecting, or transducing host cells are well-known in the art, and any appropriate method can be used.

A PTD can be purified from host cells or host cell culture medium by any method known in the art for purifying polypeptides. Examples of such methods include salt fractionation, high pressure liquid chromatography, antibody column chromatography, affinity tag column chromatography, and acrylamide gel electrophoresis. Such methods are well known to those skilled in the art.

Cell-Free Expression

A PTD can also be made by transcribing and translating a PTD coding sequence in a cell-free expression system. A coding sequence for a PTD can be linked to appropriate transcription and translation control elements by methods well known in the art. Examples of such methods include PCR, restriction enzyme digestion and ligation, and chemical synthesis. Such techniques are described, for example, in Sambrook et al. (1989) and Ausubel et al. (1989). Cell-free transcription and translation can be accomplished, for example, using components of rabbit reticulocyte or wheat germ extracts, which are available in kits from commercial suppliers such as Promega Corporation.

Antibodies to PTDs

Antibodies to a PTD can be obtained, for example, by following the methods of Harlow et al., USING ANTIBODIES: A LABORATORY MANUAL, New York: Cold Spring Harbor Laboratory Press, 1998. The antibody can be monoclonal or polyclonal. The term "antibody" means an intact immunoglobulin or a fragment thereof. Examples of fragments include Fab, F(ab')$_2$, and Fv. An antibody column for purification of a PTD by antibody column chromatography can be made and used using well known techniques and reagents in the art. For example, an IgG Orientation Kit from Pierce can be used.

Amino Acids and Amino Acid Substitutions

PTDs of the invention can contain conservative substitutions, i.e., exchange of one amino acid for another having similar properties. Examples of conservative substitutions include, but are not limited to, 1) glycine and alanine; 2) valine, isoleucine, and leucine; 3) aspartic acid and glutamic acid; 4) lysine and arginine; 5) asparagine and glutamine; and 6) serine and threonine.

A PTD can be synthesized from D- or L-amino acids. In addition, use of amino acid analogs is also contemplated. Examples of amino acid analogs includes, but is not limited to, ethyl esters, methyl esters, naphthylamides, and 7-amido-4-methyl coumarin.

Linker for PTDs

PTDs of the present invention can also have a linker attached to the N-terminus or the C-terminus. The linker is usually 0, 1, 2, 3, 4, or 5 amino acids in length and is usually a small neutral polar or non-polar amino acid such as glycine, cysteine, serine, or threonine. A preferred linker has an amino acid sequence Lys-Xaa-Xaa, wherein Xaa is a small neutral polar or nonpolar amino acid. Preferably Xaa is glycine. A preferred PTD with a lysine linker has an amino acid sequence Lys-Gly-Gly-Arg-Lys-Met-Leu-Lys-Ser-Thr-Arg-Arg-Gln-Arg-Arg (SEQ ID NO:2).

Nuclear Localization Signal

PTDs of the present invention also can comprise one or more nuclear localization signals. A preferred nuclear localization signal has an amino acid sequence Lys-Lys-Lys-Arg-Lys-Val (SEQ ID NO:3). The nuclear localization signal can be located on the amino terminus or the carboxy terminus of a PTD. A PTD comprising a nuclear localization signal can further comprise a lysine linker. The nuclear localization signal can be located upstream or down-stream of the lysine linker. Preferably, a PTD comprises a lysine linker and a nuclear localization signal located on the carboxy terminus of the peptide. A preferred PTD with a lysine linker and a nuclear localization signal has an amino acid sequence Lys-Gly-Gly-Arg-Lys-Met-Leu-Lys-Ser-Thr-Arg-Arg-Gln-Arg-Arg-Lys-Lys-Lys-Arg-Lys-Val (SEQ ID NO:4). Another preferred PTD with a lysine linker contains two nuclear localization signals. One nuclear localization signal is preferably located on the amino terminus down-stream of the lysine linker, and the second nuclear localization signal is preferably located on the carboxy terminus. A preferred PTD with a lysine linker and two nuclear localization signals has an amino acid sequence Lys-Gly-Gly-Lys-Lys-Lys-Arg-Lys-Val-Met-Leu-Lys-Ser-Thr-Arg-Arg-Gln-Arg-Arg-Lys-Lys-Lys-Arg-Lys-Val (SEQ ID NO:5).

Cargo Moiety

A cargo moiety is a small molecule, a polypeptide, a nucleic acid, or a virus. Any of these cargo moieties can be pharmaceutical agents. The small molecule also can be, for example, a radionuclide, a fluorescent marker, or a dye. A polypeptide according to the invention is a polymer of amino acids comprising two or more amino acid residues and includes peptides and proteins. The polypeptide can be, for example, an immortalization protein (e.g., SV40 large T antigen and telomerase), an anti-apoptotic protein (e.g., mutant p53 and Bcl$_x$L), an antibody, an oncogene (e.g., ras, myc, HPV E6/E7, and Adenovirus E1a), a cell cycle regulatory protein (e.g., cyclin and cyclin-dependent kinase), or an enzyme (e.g., green fluorescent protein, β-galactosidase, and chloramphenicol acetyl transferase). The nucleic acid can be, e.g., RNA, DNA, or cDNA. The sequence of the nucleic acid can be a coding or a non-coding sequence (e.g., an antisense oligonucleotide). The virus can be a whole virus or a virus core containing viral nucleic acid (i.e., packaged viral nucleic acid in the absence of a viral envelope). Examples of viruses and virus cores that can be transported include, but are not limited to, papilloma virus, adenovirus, baculovirus, retrovirus core, and Semliki virus core.

Nucleotides in the nucleic acid cargo moiety can be standard nucleotides (e.g., adenosine, cytosine, guanine, thymine, inosine, and uracil) or they can be nucleotide derivatives (e.g., biotinylated nucleotide) or analogs (e.g., phosphorothioate nucleotides). For example, the nucleic acid cargo moiety can be an antisense sequence comprising phosphorothioate nucleotides.

PTD-Cargo Moiety Complexing

A cargo moiety can be complexed to a PTD by any method known in the art and which is appropriate for a particular cargo moiety. The skilled artisan will be able to choose the appropriate method to complex a cargo moiety with a PTD. Examples of such methods include, but are not limited to, chemical cross-linking, genetic fusion, and bridging.

Chemical Cross-Linking

Either a homobifunctional cross-linker or a heterobifunctional cross-linker can be used to cross-link a PTD with a cargo moiety. The homobifunctional or heterobifunctional cross-linker can be cleavable to facilitate separation of the PTD from the cargo moiety after the PTD transports the cargo moiety across a cell membrane. Homobifunctional cross-linkers have at least two identical reactive groups. Use of homobifunctional cross-linking agents may result in self-conjugation, intramolecular cross-linking and/or polymerization. Homobifunctional cross-linkers primarily are primary amine-reactive (e.g. imidoesters, N-succinimidyl esters, isothiocynates, carboxylic acids, and sulfonyl chlorides) or sulfhydryl reactive (e.g., 2-pyridyldithio, 3-nitro-2-pyridyldithio, maleimide, vinyl sulfone, aryl halide, dinitrofluorobenzene, organomercurial, p-chloromercuribenzoate, bismaleimidohexane, 1,5-difluoro-2,4-dinitrobenzene, and 1,4-di-(3'-(2'-pyrioyldithio)-propionamido) butane). Examples of homobifunctional imidoesters include, but are not limited to dimethyladipimidate, dimethylsuberimidate, and dithiobispropionimidate. Examples of homobifunctional NHS esters include, but are not limited to, disuccinimidyl glutarate, disuccinimidyl suberate, bis(sulfosuccinimidyl) suberate, dithiobis(succinimidyl propionate), and disuccinimidyl tartarate.

Heterobifunctional cross-linkers possess two or more different reactive groups that allow for sequential conjugation with specific groups, thus minimizing undesirable polymerization or self conjugation. Some heterobifunctional cross-linkers are amine reactive at one end and sulfhydryl reactive at the other end. Examples of such cross-linking agents include, but are not limited to, succinimidyl 4-(N-maleimidomethyl) cyclohexane-1-carboxylate, m-maleimidobenzyl-N-hydroxysuccinimide ester, succinimidyl 4-(p-maleimidophenyl)-butyrate, bismaleimidohexane, and N-(g-maleimidobutyryloxy) succinimide ester.

The homobifunctional or heterobifunctional cross-linking reactions can be stopped after adding linking the homobifunctional or heterobifunctional cross linker to the PTD. The PTD with a homobifunctional or heterobifunctional cross-linking agent can be purified by methods well known in the art and used as a stock for adding cargo moieties. Such purified PTD with the attached homobifunctional or heterobifunctional cross-linking reagent can be stored, for example at −20° C. in aliquots and subsequently thawed. Once thawed a cargo moiety can be added by completing the cross-linking reaction.

Genetic Fusion

Genetic fusions can be generated by linking a coding sequence for a PTD in-frame with a coding sequence for a polypeptide cargo moiety. Many methods exist in the art for linking coding sequences together. Exemplary methods include, but are not limited to, polymerase chain reaction (PCR), stitch PCR, and restriction endonuclease digestion and ligation. For example, a coding sequence for a PTD can be added to the 5'-end of a PCR primer for a cargo moiety of choice; after PCR, the coding sequences for the PTD and the polypeptide cargo moiety will be linked together. The skilled artisan will know how to ensure that the reading frames of the PTD and the cargo moiety are in frame and where transcriptional control sequences (e.g., start codon and stop codon) should be placed. A protease cleavage site can be included between the PTD and the cargo moiety. Examples of such protease cleavage sites include, but are not limited to Factor Xa and tobacco etch virus (TEV) protease.

Bridging Molecules

PTDs and cargo moieties can be complexed using pairs of bridging molecules. Examples of such pairs include, but are not limited to, (a) streptavidin and biotin, (b) glutathione and glutathione-S-transferase, and (c) polyhistidine and an affinity chromatography reagent (e.g., tetradentate nitrilotriacetic acid (NTA) or iminodiacetic acid (IDA)), which interact through an ion such as $Ni^{+2}$. A PTD can be linked to either member of the pair, and a cargo is linked to the other bridging molecule. For example, if the PTD is linked to glutathione-S-transferase then the cargo is linked to glutathione. Preferably, the PTD is linked to streptavidin and the cargo is linked to biotin. The PTD and the streptavidin can be linked by any method known in the art for linking a peptide and a bridging molecule. Examples of such methods include, but are not limited to, chemical cross-linking or genetic fusion. Preferably the PTD and streptavidin are linked by genetic fusion. The cargo is then linked to biotin by any method known in the art for biotinylating small molecules, proteins, or nucleic acids, such as chemical cross-linking. The PTD cargo moiety complex can be formed by contacting the PTD-streptavidin with the biotinylated cargo moiety.

In another embodiment, glutathione and glutathione-S-transferase are used as the pair of bridging molecules. In this case, the PTD is preferably linked to the glutathione-S-transferase and the cargo is linked to the glutathione. The PTD and the glutathione-S-transferase can be linked by any method described above, although genetic fusion is preferred. The cargo is linked to the glutathione by any method known in the art for linking glutathione to small molecules, proteins, or nucleic acids. An example of such method is chemical cross-linking. The PTD-cargo moiety complex can be formed by contacting the PTD-glutathione-S-transferase with the glutathione-linked cargo moiety.

In yet another embodiment, an affinity chromatography reagent and polyhistidine are used as the pair of bridging molecules. In this case the PTD is preferably linked to the affinity chromatography reagent. The affinity chromatography reagents bind ions such as Ni+2 with different affinities. NTA binds $Ni^{+2}$ with stronger affinity that IDA. A skilled artisan will be able to choose which binding affinity is desired for a particular application. The PTD and affinity chromatography reagent can be linked by, for example, chemical cross linking. The cargo is linked to polyhistidine by any method known in the art for linking polyhistidine to small molecules, proteins, or nucleic acids. The PTD-cargo moiety complex can be formed by contacting the PTD-affinity chromatography reagent complex with the polyhistidine-linked cargo moiety in the presence of an ion such as $Ni^{+2}$.

Orientation of PTD and Cargo Moiety

A PTD and cargo moiety can be complexed chemically or using pairs of bridging molecules at any position on either the PTD or the cargo moiety, providing that functionality of either the PTD or cargo moiety is not destroyed. For example, a cross-linking agent will react with appropriate functional groups located at the amino-terminus or carboxy-terminus (for proteins), at the 5' end or 3' end (for nucleic acids), or throughout the molecule. A skilled artisan will be able to determine if the respective parts of the PTD-cargo moiety complex retains biological activity. The PTD retains biological activity if it can transport cargo into a cell. Transport activity can be ascertained, for example, by adding the PTD cargo moiety complex to cells and assaying the cells to determine if the cargo moiety was delivered across the cell membrane. One skilled in the art can determine if the cargo is located intracellularly using methods well known in the art (e.g., immunohistochemical staining). The cargo moiety can be assayed for activity using a method acceptable for the type of cargo moiety (e.g., an enzyme assay for an enzyme, a transformation assay for an oncoprotein, an anti-apoptotic assay for an anti-apoptosis protein, and an immortalization assay for an immortalization protein). These assays are well known in the art and are described in Sambrook et al., 1989 and Ausubel et al., 1989.

If the PTD and polypeptide cargo moiety are genetically linked, the polypeptide cargo moiety can be complexed to either the amino terminus of the PTD or to the carboxy-terminus of the PTD. Preferably, the polypeptide cargo moiety is complexed to the carboxy-terminus of the PTD.

Cells

PTDs of the invention can transport a cargo moiety into a variety of mammalian, amphibian, reptilian, avian, or insect cells. Cells can be primary cells or cell lines. Mammalian cells can be, e.g., human, monkey, rat, mouse, dog, cow, pig, horse, hamster, and rabbit. Examples of amphibian cells include, but are not limited to, frog and salamander. Reptilian cells include, but are not limited to, snakes and lizards. Examples of avian cells include, but are not limited to, chickens, quails, and ducks. Insect cells can be, for example, *Drosophila* and *Lepidoptera* (e.g., fall army worm). Primary cells from mammalians include, but are not limited to, adipocytes, astrocytes, cardiac muscle cells, chondrocytes, endothelial cells, epithelial cells, fibroblasts, gangliocytes, glandular cells, glial cells, hematopoietic cells, hepatocytes, keratinocytes, myoblasts, neural cells, osteoblasts, ovary cells, pancreatic beta cells, renal cells, smooth muscle cells, and striated muscle cells. Cell lines include 182-PF-SK, 184A1, 2H-11, 2F-2B, 293, 27FR, 28SC, 3B-11, 4T1, 7F2, A172, A375.S2, A-253, A-431, ARH-77, AHH-1, AML-193, A-10, BS-C-1, BHK-21, BE(2)-117, BCE, BJ, B16-F0, BT-20, BT-474, BLP-1, BRL-3A, BLO-11, CTX-TNA2, C8-D30, C8-S, CPAE, CPA47, CHO-K1, CV-1, C6, CHP-212, C8-B4, C166, C-211, CCD-25Sk, C32, CTPS, C1-S1, C127, CF41-Mg, CMMT, CAMA-1, C5/MJ, C3A, C2C12, COS-1, COS-7, Dempsey, Detroit 532, Daudi, EBTr(NBL-4), EOMA, EJG, E Derm, EB, EM-9, FBHE, FL, F98, G-361, GK-5, GDM-1, G-7, G-8, HIG-82, H9c2 (2-1), HUV-EC-C, HeLa, HaK, HEp-2, HT-1080, HG-261, HEL-299, H2.35, HEp-G2, H4, HAAE-1, HAAE-2, HUVE-12, Hs27, Hs68, HL-60, H4TG, Hepal-6, IMR-32, IP-1B, J1-31, J2 3T3, JC, JHK3, KB, K-562, KG-1, L-132, LLC-MK2, LA7, LMH, L8, MDBK, MO59K, Mar Vin, MM5MTC, MCF7, MoB, MOLT-3, MH1C1, NIH 3T3, Neuro-2a, NB41A3, NIE-115, NMVMG, NMU, OV-90, P19, PFSK-1, PC-12, PaCa-2, PANC-1, QM-7, RF/6A, RK13, rat1, rat2, RG2, RT101, RBA, Rn2T, RBL-1, Swiss SFMF, SK-N-AS, SH-SY5Y, Sf1Ep, SW-13, SW-527, SK-BR-3, SNU449, SK-Hep1, Snyder, Sf9, Sf21, T98G, TH-1, Toledo, UV41, Vero, WS6, WR-21, XP17BE, Y-1, ZR-75-1, and ZR-75-30.

Reversible Immortalization

Normal healthy cells will only undergo a fixed number of divisions before they senesce and no longer replicate. Immortalization proteins are proteins that prevent a cell from senescing. Examples include, but are not limited to, SV40 large T antigen and telomerase. Immortalized cells, however, can divide many times after their normal counterparts senesce.

A complex of a PTD and an immortalization protein can be used to reversibly immortalize a cell in culture. Preferably the PTD has an amino acid sequence Arg-Lys-Met-Leu-Lys-Ser-Thr-Arg-Arg-Gln-Arg-Arg (SEQ ID NO:1), Lys-Gly-Gly-Arg-Lys-Met-Leu-Lys-Ser-Thr-Arg-Arg-Gln-Arg-Arg (SEQ ID NO:2), Lys-Gly-Gly-Arg-Lys-Met-Leu-Lys-Ser-Thr-Arg-Arg-Gln-Arg-Arg-Lys-Lys-Lys-Arg-Val (SEQ ID NO:4), or Lys-Gly-Gly-Lys-Lys-Lys-Arg-Val-Arg-Lys-Met-Leu-Lys-Ser-Thr-Arg-Arg-Gln-Arg-Arg-Lys-Lys-Lys-Arg-Val (SEQ ID NO:5), and the immortalization cargo moiety is SV40 large T antigen or telomerase. A cell can be contacted in vitro with the complex. The PTD cargo moiety complex can be added to the cell culture medium or can be included in medium that is supplied to the cell. Preferably the complex is present in an amount greater than about 1 nM of the PTD. For example, the complex can be present in an amount from about 10 nM to about 1000 nM (i.e., 10, 20, 30, 40, 50, 100, 200, 300, 400, 500, 600, 700, 800, 900, or 1000 nM), more preferably from about 10 nM to about 500 nM, even more preferably from about 10 nM to about 100 nM, and yet even more preferably from about 10 nM to about 50 nM of the PTD. The PTD will transport the immortalizing peptide across the cell membrane, and the immortalizing protein will immortalize the cell. While it continues to be cultured in the presence of the complex, the cell will be immortalized, i.e., it will continue to divide. If the complex is removed from the medium, the cell will no longer be immortalized.

Methods of Increasing Cell Viability

A complex of a PTD and an anti-apoptotic protein can be used to increase cell viability. Preferably the PTD has an amino acid sequence Arg-Lys-Met-Leu-Lys-Ser-Thr-Arg-Arg-Gln-Arg-Arg (SEQ ID NO:1), Lys-Gly-Gly-Arg-Lys-Met-Leu-Lys-Ser-Thr-Arg-Arg-Gln-Arg-Arg (SEQ ID NO:2), Lys-Gly-Gly-Arg-Lys-Met-Leu-Lys-Ser-Thr-Arg-Arg-Gln-Arg-Arg-Lys-Lys-Lys-Arg-Val (SEQ ID NO:4), or Lys-Gly-Gly-Lys-Lys-Lys-Arg-Val-Arg-Lys-Met-Leu-Lys-Ser-Thr-Arg-Arg-Gln-Arg-Arg-Lys-Lys-Lys-Arg-Val (SEQ ID NO:5). A cell can be contacted in vitro with the complex. The PTD cargo moiety complex can be added to the cell culture medium or can be included in medium that is supplied to the cell. Preferably the complex is present in an amount greater than about 1 nM of the PTD. For example, the complex can be present in an amount from about 10 nM to about 1000 nM (i.e., 10, 20, 30, 40, 50, 100, 200, 300, 400, 500, 600, 700, 800, 900, or 1000 nM), more preferably from about 10 nM to about 500 nM, even more preferably from about 10 nM to about 100 nM, and yet even more preferably from about 10 nM to about 50 nM of the PTD. The PTD will transport the anti-apoptotic cargo moiety across the cell membrane and increase cell viability by inhibiting apoptosis. While it continues to be cultured in the presence of the complex, the cell will have increased viability. Anti-apoptotic agents include, but are not limited to, mutant p53 and $Bcl_xL$.

Kits

A PTD and a cargo moiety can be supplied in a kit. The PTD is preferably a PTD-streptavidin fusion protein, and the streptavidin is preferably located at on the carboxy terminus of the PTD. The PTD preferably has an amino acid sequence Arg-Lys-Met-Leu-Lys-Ser-Thr-Arg-Arg-Gln-Arg-Arg (SEQ ID NO:1), Lys-Gly-Gly-Arg-Lys-Met-Leu-Lys-Ser-Thr-Arg-Arg-Gln-Arg-Arg (SEQ ID NO:2), Lys-Gly-Gly-Arg-Lys-Met-Leu-Lys-Ser-Thr-Arg-Arg-Gln-Arg-Arg-Lys-Lys-Lys-Arg-Val (SEQ ID NO:4), or Lys-Gly-Gly-Lys-Lys-Lys-Arg-Val-Arg-Lys-Met-Leu-Lys-Ser-Thr-Arg-Arg-Gln-Arg-Arg-Lys-Lys-Lys-Arg-Val (SEQ ID NO:5). The cargo moiety can be a small molecule (e.g., a radionuclide, a fluorescent marker, a dye, or a pharmaceutical agent), a protein (e.g., an immortalizing agent, an anti-apoptotic agent, an enzyme, an oncoprotein, a cell cycle regulatory protein, or an antibody), a nucleic acid (e.g., RNA, DNA, and cDNA), or a virus (e.g., papilloma virus, adenovirus, baculovirus, retrovirus core, or Semliki virus core). The cargo moiety preferably is biotinylated. The PTD and cargo moiety can be supplied in single or divided aliquots, in single or divided containers. Written instructions can be included for assembling a PTD-cargo moiety complex and/ or for using the complex. The instructions can be on the label or container. The instructions may simply refer a reader to another location such as a website or other information source.

All patents, patent applications, and references cited in this application are incorporated herein by reference in their entirety.

The following examples are offered by way of illustration and do not limit the invention.

EXAMPLES

Example 1

Effect of Biotin Location on PTD Transduction Efficiency

To determine the effect of biotin location on transduction efficiency, biotin was added to either the amino terminus or the carboxy terminus of three PTDs. A (Gly)₃ linker was added to the amino terminus for N-terminal biotinylated peptides. For C-terminal biotinylation, the last glycine in the C-terminal linker was replaced by lysine. The side chain of lysine was used for the attachment of the biotin group. A peptide with negligible transduction activity (Mi et al., Mol. Ther., 2:339–347, 2000) (SEQ ID NO:6) was used as a negative control. The amino acid sequences of the PTDs and the biotin locations tested are listed in Table 1. PTDs and β-galactosidase were complexed together with a streptavidin-biotin bridge.

TABLE 1

Biotin-Gly-Gly-Ala-Arg-Pro-Leu-Glu-   (SEQ ID NO:6)
His-Gly-Ser-Asp-Lys-Ala-Thr (Negative Control)

Biotin-Gly-Gly-Gly-Tyr-Gly-Arg-Lys-   (SEQ ID NO:7)
Lys-Arg-Arg-Gln-Arg-Arg-Arg (Biotin-Tat)

Tyr-Gly-Arg-Lys-Lys-Arg-Arg-Gln-Arg-  SEQ ID NO:8)
Arg-Arg-Gly-Gly-Lys-Biotin (Tat-Biotin)

TABLE 1-continued

Biotin-Gly-Gly-Gly-Tyr-Ala-Arg-Ala-   SEQ ID NO:9)
Ala-Ala-Arg-Gln-Ala-Arg-Ala (Biotin-DP4)

Tyr-Ala-Arg-Ala-Ala-Ala-Arg-Gln-Ala-  SEQ ID NO:10)
Arg-Ala-Gly-Gly-Lys-Biotin (DP4-Biotin)

Arg-Arg-Gln-Arg-Arg-Thr-Ser-Lys-Leu-  (SEQ ID NO:11)
Met-Lys-Arg-Gly-Gly-Lys-Biotin (RP5-Biotin)

Biotin-Gly-Gly-Gly-Arg-Arg-Gln-Arg-   (SEQ ID NO:12)
Arg-Thr-Ser-Lys-Leu-Met-Lys-Arg (Biotin-RP5)

To test for transduction efficiency, 293 HEK cells were seeded into a 96-well plate at approximately 4500 cells/well and incubated overnight. To prepare peptide complexes, equimolar concentrations of biotinylated PTD and streptavidin-crosslinked β-galactosidase were mixed and diluted in cell culture medium. The mixtures were incubated for 30 minutes at 37° C. to allow formation of complexes. Each complex was added to a final concentration of 50 nM and incubated for 30 minutes at 37° C. To assay for β-galactosidase activity, the cells were washed 3 times with PBS and were lysed with 100 μl of assay reagent (Pierce). Cell lysates were incubated for 30 minutes at 37° C., and the reaction was stopped by adding 150 μl stop solution (Pierce). The absorbance at 405 mn was measured on a Wallac Victor spectroluminometer. The results are shown in FIG. 1.

FIG. 1 shows the absorbance at 405 nm for the cells transduced with each of the different complexes. The results demonstrate a position effect for the biotin. When biotin was added to the carboxy terminus of the PTD, the transduction efficiency was higher, as indicated by the presence of more β-galactosidase in the cell lysates. Peptides having the amino acid sequences shown in SEQ ID NOS:8 and 9 did not function as a PTD, because the amount of β-galactosidase present in the cell lysate was less than or equal to the negative control (SEQ ID NO:6).

Example 2

Peptide Transduction into Primary Cells

The ability of the PTDs to translocate β-galactosidase into human primary (HUVEC) cells was investigated. The transduction efficiency as a function of time exposure to the PTD-β-galactosidase complexes was also analyzed.

To test for transduction efficiency, HUVEC cells were seeded into a 96-well plate as described in Example 1. PTD-β-galactosidase complexes were prepared as described in Example 1. Each complex was added to a final concentration of 50 nM to the wells of the 96-well plate. The cells were incubated for 7, 14, 24, 35, or 45 minutes at 37° C. before being washed 3 times with PBS. Following the last PBS wash, the cells were lysed with 100 μl of assay reagent (Pierce) and incubated at 37° C. for 30 minutes. The lysis reaction was stopped by adding 150 μl stop solution (Pierce), and the absorbance at 405 nm was measured on a Wallac Victor spectroluminometer. The results are shown in FIG. 2.

Figure 2:
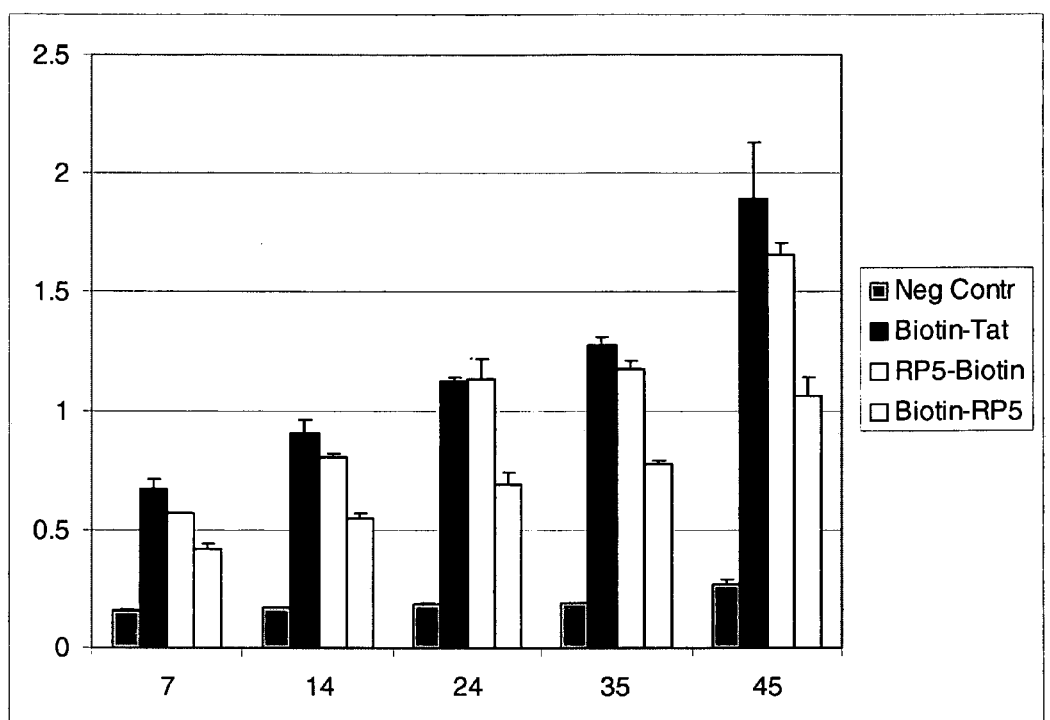
FIG. 2 shows the effect of exposure of PTD complexes to cells on transport of β-galactosidase across a cell membrane.

FIG. 2 shows that primary HUVEC cells can be transduced with the PTDs. In addition, transduction can be detected as early as 7 minutes after exposure to the PTD. There is a linear correlation between the intracellular β-galactosidase accumulation and the time of exposure to the PTD complexes. No saturation was detected during the 45 minute incubation.

Figure 3:
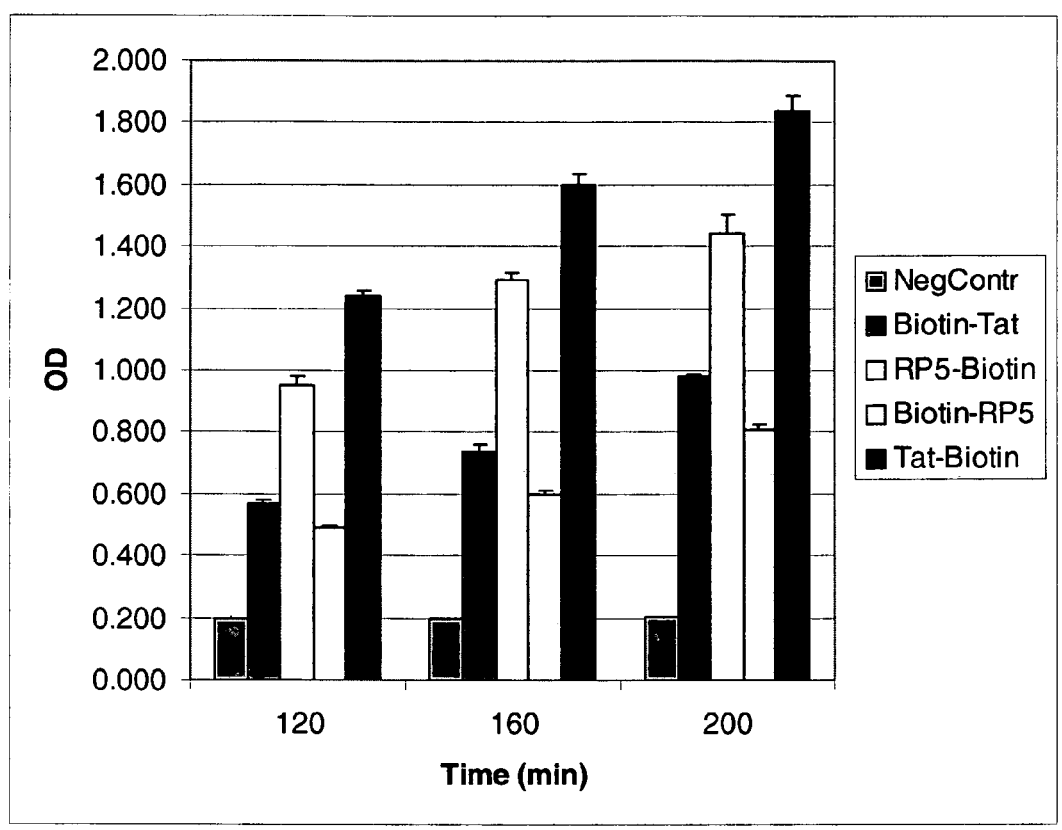
FIG. 3 shows the effect of extended exposure of PTD complexes to cells on transport of β-galactosidase across a cell membrane.

Because saturation was not detected in a 45 minute incubation, the effect of extended incubation (up to 200 minutes) was analyzed. Two types of primary cells were used: primary dermal fibroblasts and primary HUVEC cells. The cells were seeded as described above and 12.5 nM final concentration of PTD-β-galactosidase complex was added to each well. The cells were incubated at 37° C. for 120, 160, or 200 minutes. The cells were washed and lysed as described above. The lysis reaction was stopped, and the absorbance at 405 nm was determined. The results for primary dermal fibroblasts (FIG. 3) and primary HUVEC cells indicate that no detectable saturation of intracellular accumulation of the PTD complexes occurred up to 200 minutes of incubation.

Example 3

Effects of Temperature on Transduction Efficiency

Figure 4:
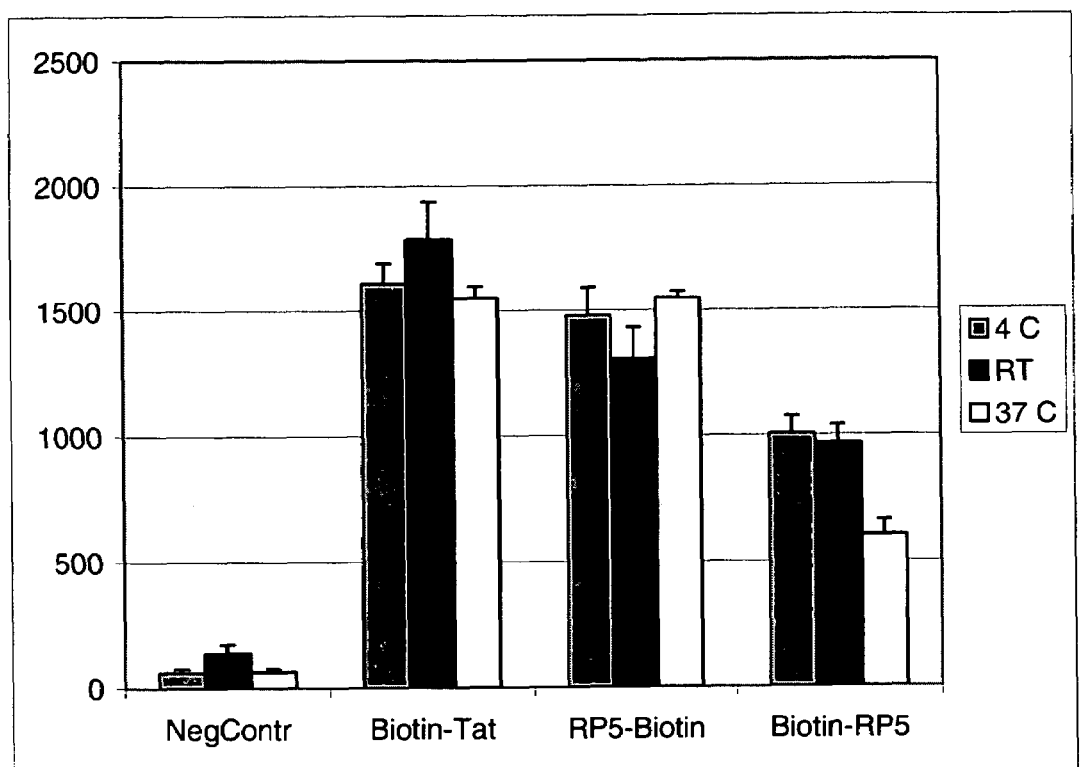
FIG. 4 shows the effects of temperature on PTD-mediated transport of β-galactosidase.

The activity of the PTD-β-galactosidase complexes was compared at 4° C., room temperature (RT), and 37° C. to analyze the effects of temperature on the transduction efficiency. HUVEC cells were cultured as described in Example 2, and PTD-β-galactosidase complexes (described in Example 1) were added to the cultures at 50 nM final concentration. Following addition of the PTD-β-galactosidase complexes, the cells were incubated for 30 minutes at the specified temperature. The cells were washed and lysed as described above. The lysis reaction was stopped, and the absorbance at 405 nm was measured. The results are shown in FIG. 4. FIG. 4 shows that the transduction activity of the PTDs is independent of temperature.

Example 4

Transduction Efficiency of Inverted Isomers of PTDs

Figure 5:
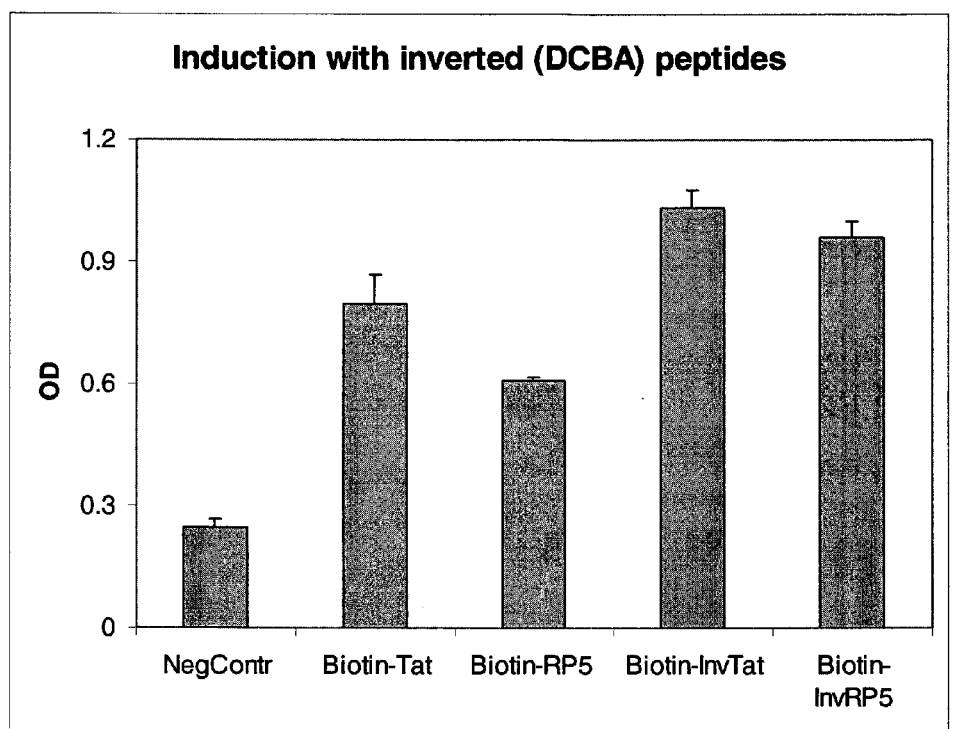
FIG. 5 shows the effects of chirality on PTD-meditated transport of β-galactosidase.

N-terminally biotinylated direct and inverted isomers were compared to determine the transduction efficiency of inverted isomers of PTDs. Table 2 lists the sequences of PTDs used. PTDs and β-galactosidase were complexed together with a streptavidin-biotin bridge. NIH 3T3 cells were seeded into a 96-well plate and incubated as described above. The PTD-β-galactosidase complexes were formed (as described in Example 1) and added to a final concentration of 12.5 nM. The cells were incubated for 1 hour at 37° C. and lysed as described above. The lysis reaction was stopped and the absorbance at 405 nm was measured. The results are shown in FIG. 5. The transduction activity of inverted isomers is stronger than the transduction activity of direct PTDs.

TABLE 2

Biotin-Lys-Gly-Gly-Arg-Arg-Arg-Gln- (SEQ ID NO:13)
Arg-Arg-Lys-Lys-Arg-Gly-Tyr (Biotin-Lys-InvTat)

TABLE 2-continued

Biotin-Lys-Gly-Gly-Arg-Lys-Met-Leu- (SEQ ID NO:14)
Lys-Ser-Thr-Arg-Arg-Gln-Arg-Arg (Biotin-Lys-InvRP5)

Biotin-Gly-Gly-Gly-Arg-Arg-Arg-Gln- (SEQ ID NO:15)
Arg-Arg-Lys-Lys-Arg-Gly-Tyr (Biotin-InvTat)

Biotin-Gly-Gly-Gly-Arg-Lys-Met-Leu- (SEQ ID NO:16)
Lys-Ser-Thr-Arg-Arg-Gln-Arg-Arg (Biotin-InvRP5)

Biotin-Lys-Gly-Gly-Arg-Arg-Gln-Arg- (SEQ ID NO:17)
Arg-Thr-Ser-Lys-Leu-Met-Lys-Arg (Biotin-Lys-RP5)

Example 5

Effects of an Amino Terminal Lysine on Transduction Efficiency

Figure 6:
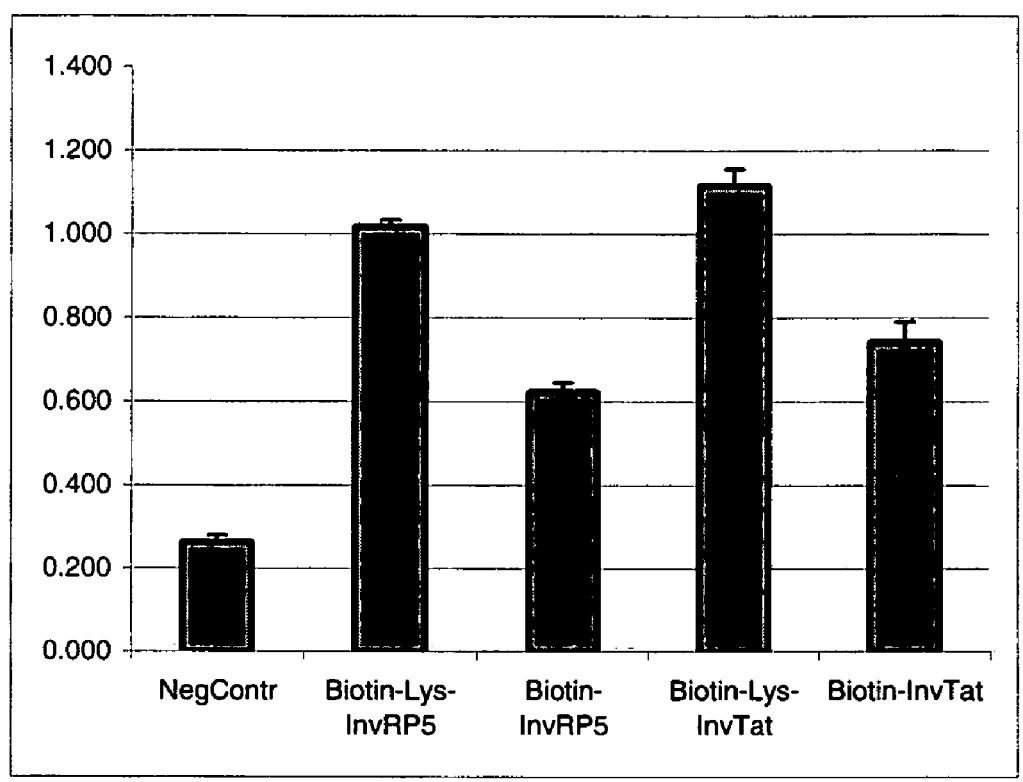
FIG. 6 shows the effects of an amino terminal lysine residue on PTD transport.

The activities of 2 PTDs were compared to determine if the introduction of a lysine residue juxtaposed to the biotin moiety affects transduction activity. The amino acid sequences of the peptides are listed in Table 2. The pairs of peptides differed by a glycine to lysine substitution within the biotin peptide linker. PTDs and β-galactosidase were complexed together with a streptavidin-biotin bridge. NIH 3T3 cells were seeded as described above. The PTD-β-galactosidase complex was added to a final concentration of 20 nM, and the cells were incubated for 1 hour at 37° C. Following incubation, the cells were washed 3 times in PBS and lysed as described above. The lysis reaction was stopped, and the absorbance at 405 nm was measured. The results are shown in FIG. 6. The presence of a lysine residue juxtaposed to the biotin caused about a two-fold enhancement in transduction activity.

Figure 7:
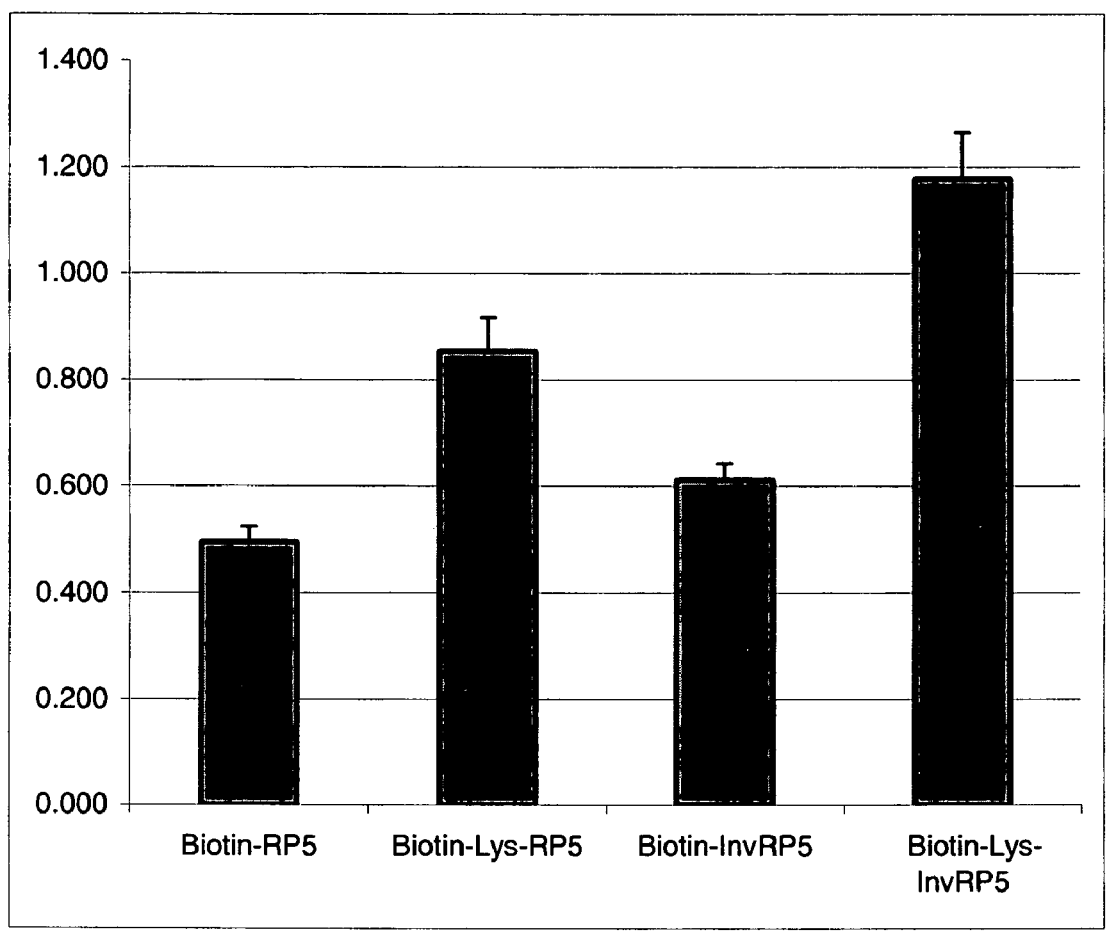
FIG. 7 shows a comparison of transduction activities of direct and inverted isomers of PTDs.

To further study the role of the lysine residue located in the biotin linker, the indirect PTDs and the direct PTDs with a lysine residue in the linker were compared. The cells used were NIH 3T3 cells, and the final concentration of the PTD complex was 12.5 nM. The assay was conducted as described above. The results are shown in FIG. 7. Introduction of a lysine residue improved transduction efficiency by as much as 72%.

Example 6

Percent of Cells Transduced with PTD

To determine the efficiency of transduction based on the percentage of cells that receive the reporter protein, cells were assayed by histochemical staining for the reporter protein. The purpose of this experiment was to ensure that the β-galactosidase activity in total cell lysates did not originate from PTD complexes precipitated on the plastic surfaces of the cell culture plates.

Figure 8A:
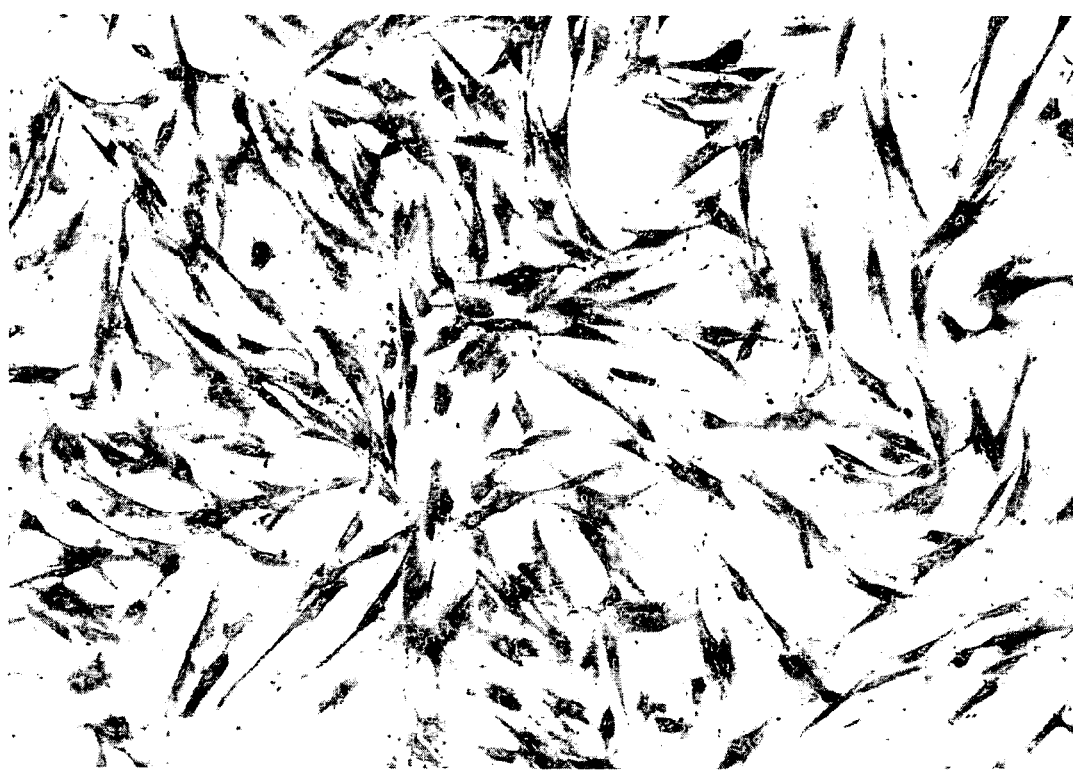
FIG. 8A shows human dermal fibroblasts transduced with a PTD-cargo moiety complex comprising the polypeptide sequence shown in SEQ ID NO:8 and streptavidin-linked β-galactosidase.
Figure 8B:
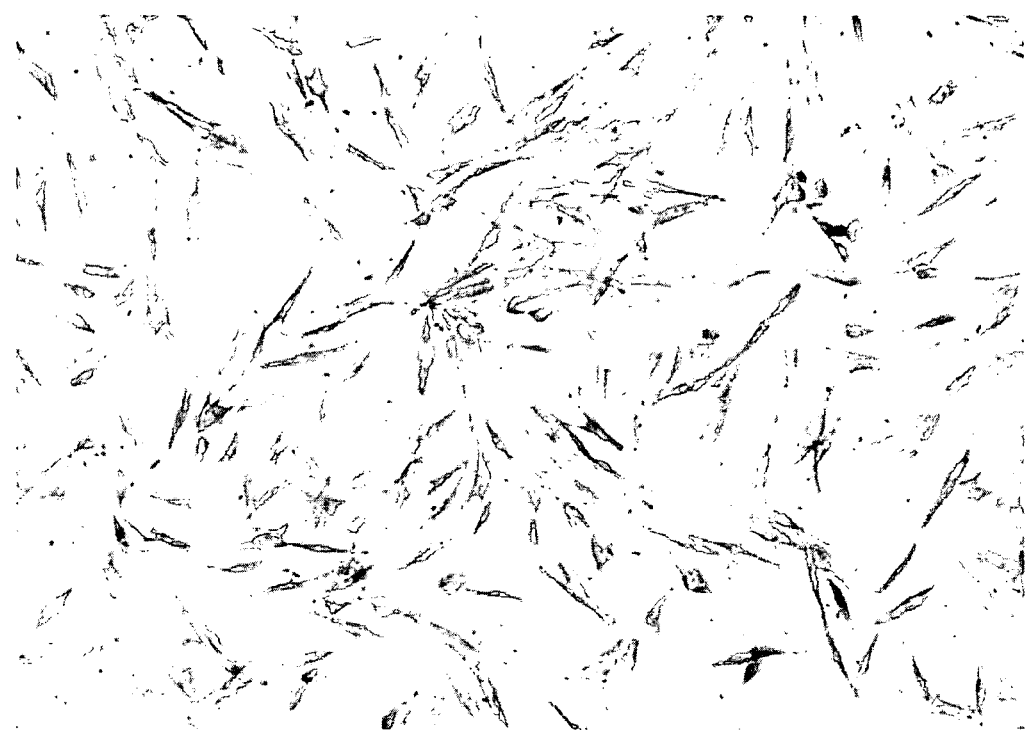
FIG. 8B shows human dermal fibroblasts transduced with a PTD-cargo moiety complex comprising the polypeptide sequence shown in SEQ ID NO:7 and streptavidin-linked β-galactosidase.

HUVEC and human dermal fibroblast cells were each seeded at 40,000 per well of a 24-well plate and incubated overnight. PTD complexes (SEQ ID NO:7-streptavidin-β-galactosidase or SEQ ID NO:6-streptavidin-β-galactosidase) were added to the wells at a final concentration of 50 nM and incubated for 1 hour at 37° C. The cells were washed 3 times in PBS, fixed, and stained for β-galactosidase using a β-galactosidase staining set (Roche) according to the manufacturer's instructions. Following development of β-galactosidase activity, the cells were washed with PBS and visualized by light microscopy. FIG. 8A shows human dermal fibroblasts transduced with a PTD-cargo moiety complex comprising the polypeptide sequence shown in SEQ ID NO:8 and streptavidin-linked β-galactosidase. FIG. 8B shows human dermal fibroblasts transduced with a PTD-cargo moiety complex comprising the polypeptide sequence shown in SEQ ID NO:7 and streptavidin-linked β-galactosidase. The results demonstrate that the cells were positive for the β-galactosidase reporter protein and that the β-galactosidase activity in the lysate assays was not the result of the complex attaching to the plastic. The results also demonstrate that transduction with a C-terminal biotinylated PTD was stronger that the N-terminally biotinylated peptide.

Example 7

Intracellular Localization of the PTD Complex

To determine the intracellular location of the complex, cells were immunostained for streptavidin. NIH 3T3 cells were seeded into 24-well tissue culture plates and incubated overnight. The cells were treated with 20 nM PTD-cargo moiety complex comprising the polypeptide sequence shown in SEQ ID NO:14 and streptavidin-linked β-galactosidase for 1 hour at 37° C. The cells were washed 3 times with PBS, and non-specific binding was blocked by a 30 minute incubation with normal goat serum at room temperature. Mouse anti-streptavidin monoclonal antibody (Monosan, Catalog No. 5043) was diluted to 1 μg/ml with PBS containing 20% normal goat serum. The diluted monoclonal antibody was added to the cells, and the cells were incubated for 1 hour at room temperature.

Figure 9A:
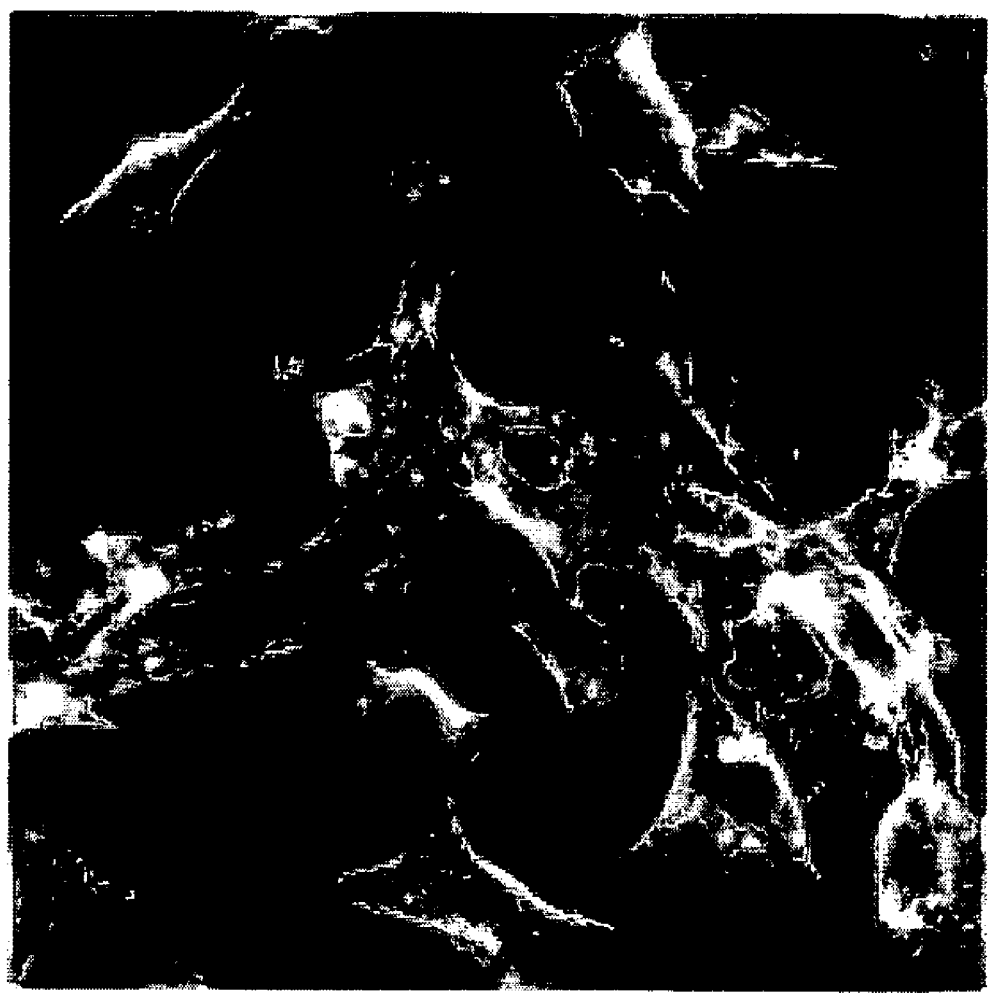
FIG. 9A shows NIH 3T3 cells transduced with a PTD-cargo moiety complex comprising the polypeptide sequence shown in SEQ ID NO:14 and streptavidin-linked β-galactosidase and stained for streptavidin using an anti-streptavidin antibody. The cells were visualized with fluorescent microscopy.
Figure 9B:
FIG. 9B shows the NIH 3T3 cells from FIG. 9A visualized with phase contrast microscopy.

The cells were washed 3 times with PBS and a secondary Alexa Fluor 568 conjugated goat anti-mouse IgG (Molecular Probes, Catalog No. A-11019) was diluted 1:200 in PBS with 20% normal goat serum. Following a 30 minute incubation at room temperature, the cells were washed 3 times with PBS and visualized by fluorescent microscopy. The results are shown in FIG. 9A. FIG. 9B shows the same field of cells as FIG. 9A, but visualized by phase contrast microscopy. The complex was localized to the cytoplasm.

Example 8

Delivery of Alkaline-Phosphatase by PTD Transduction

Figure 10:
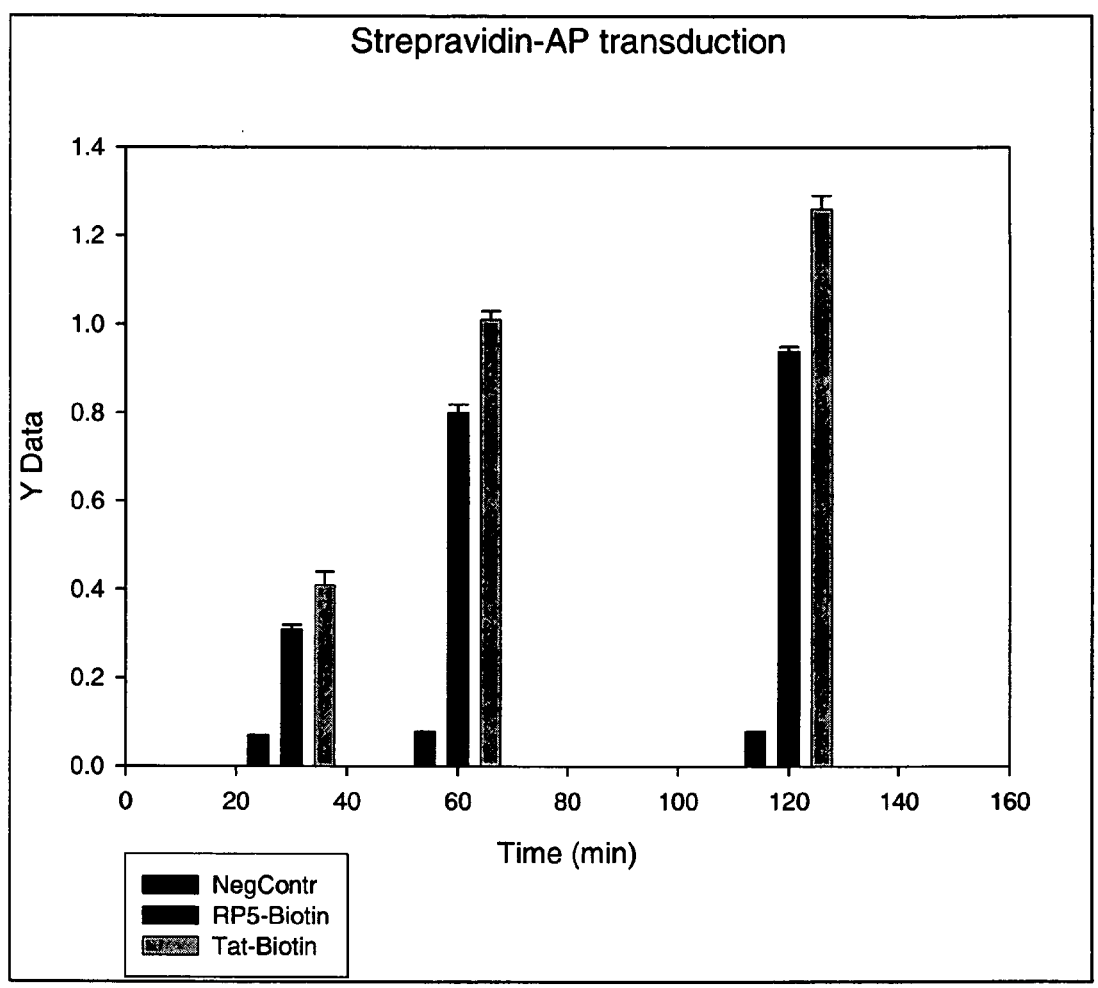
FIG. 10 shows the effect of extended exposure of PTD complexes to cells on transport of alkaline phosphatase.

Transduction of an alternative reporter protein was analyzed to exclude the possibility that the above results were restricted to the β-galactosidase reporter protein. Alkaline phosphatase was complexed to the C-terminus of PTDs (Table 2) by a streptavidin-biotin bridge, and transduced into NIH 3T3 cells using the methods described above. Following washing and lysis, alkaline phosphatase activity was determined. FIG. 10 shows that alkaline phosphatase also was efficiently delivered into cells.

Example 9

Cytotoxicity of PTDs on Cell Growth

PTDs (SEQ ID NOS:7 and 10), in the absence of a cargo moiety, were added to NIH 3T3 cultures at final concentrations ranging from 0–1000 nM to determine if the PTDs were cytotoxic. NIH 3T3 cells were seeded and incubated overnight, and the peptides were added to the cultures. The cells were incubated for 48 hours, and cell viability was determined using an Alamar blue assay.

Figure 11A:
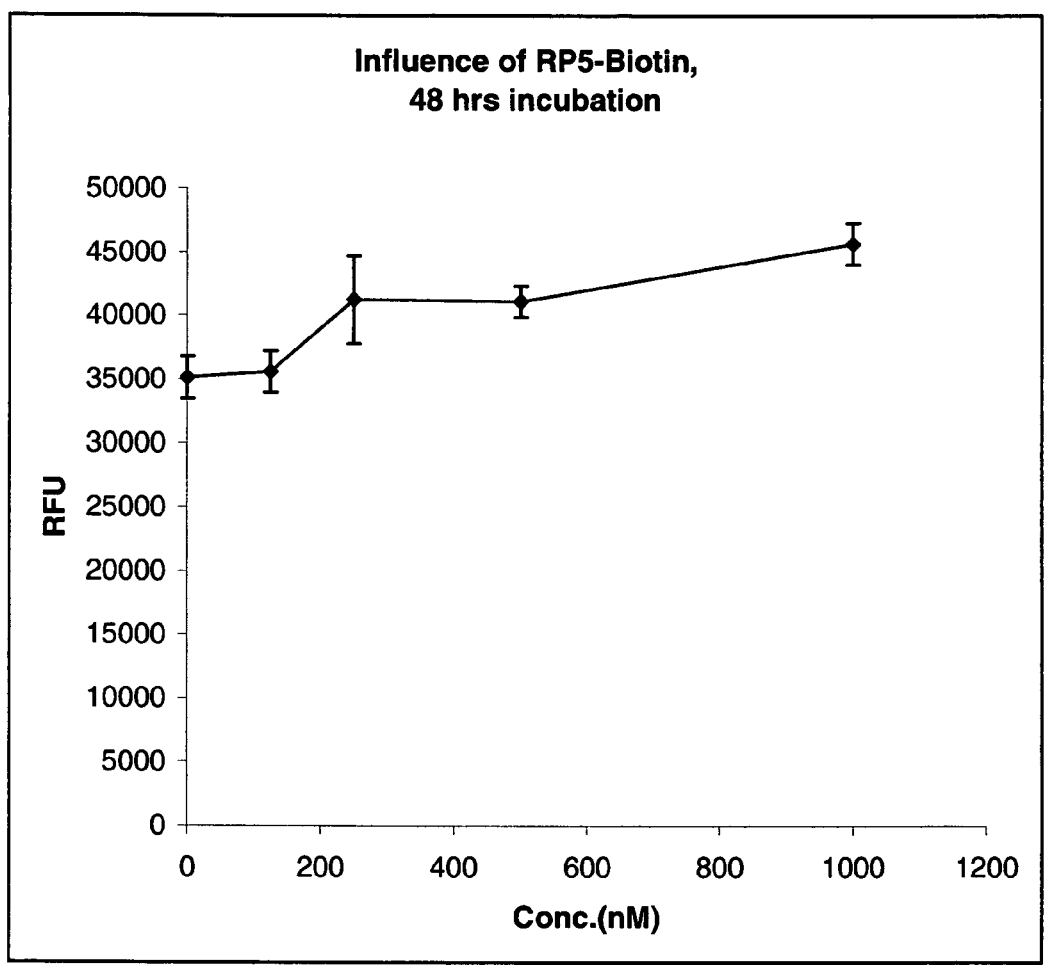
FIG. 11A shows the effect of PTD concentration on cell viability in cell culture. The relative number of viable cells was determined using Alamar Blue staining.
Figure 11B:
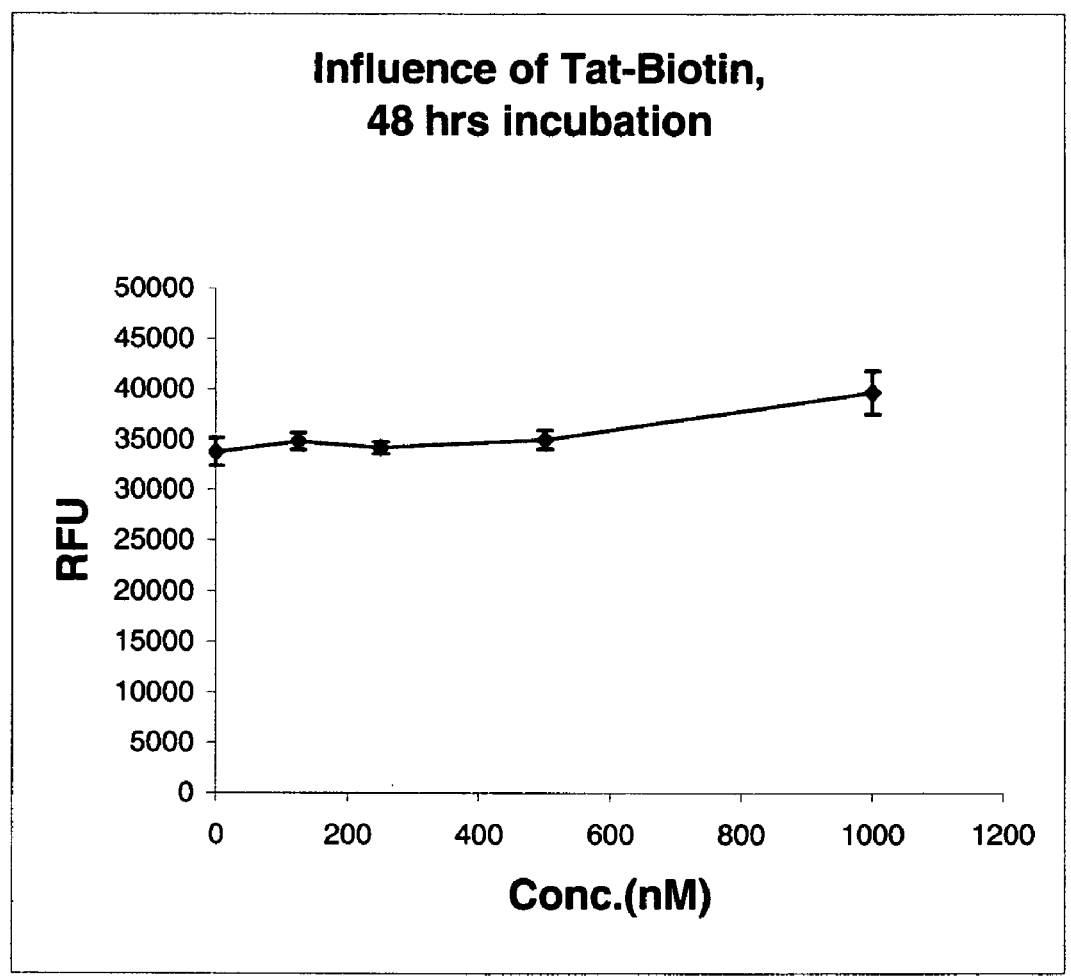
FIG. 11B shows the effect of PTD concentration on cell viability in cell culture. The relative number of viable cells was determined using Alamar Blue staining.

The results for the PTD shown in SEQ ID NO:1 are shown in FIG. 11A. The results for the PTD shown in SEQ ID NO:8 are shown in FIG. 11B. Concentrations of either PTD in the nanomolar range did not inhibit cell growth.

Example 10

Nuclear Localization of PTD-Cargo Moiety Complexes

The transport activities of PTDs were compared to determine if introduction of a nuclear localization signal affect translocation of a PTD-cargo moiety complex. The amino acid sequences of the PTDs are listed in Table 3. The cargo moiety was streptavidin-linked β-galactosidase. The cargo moiety was streptavidin-linked β-galactosidase. The peptides differed by the position of the nuclear localization signal. The nuclear localization signal was located on the amino terminus (down-stream of a lysine linker) or the carboxy terminus. NIH 3T3 cells were seeded as described above. Each PTD complex was added to a final concentration of 20 nM, and the cells were incubated for 1 hour at 37° C. Following incubation, the cells were washed 3 times in PBS and assayed for nuclear localization of β-galactosidase. β-galactosidase activity was measured at 405 nm in a colorimetric assay.

Figure 12:
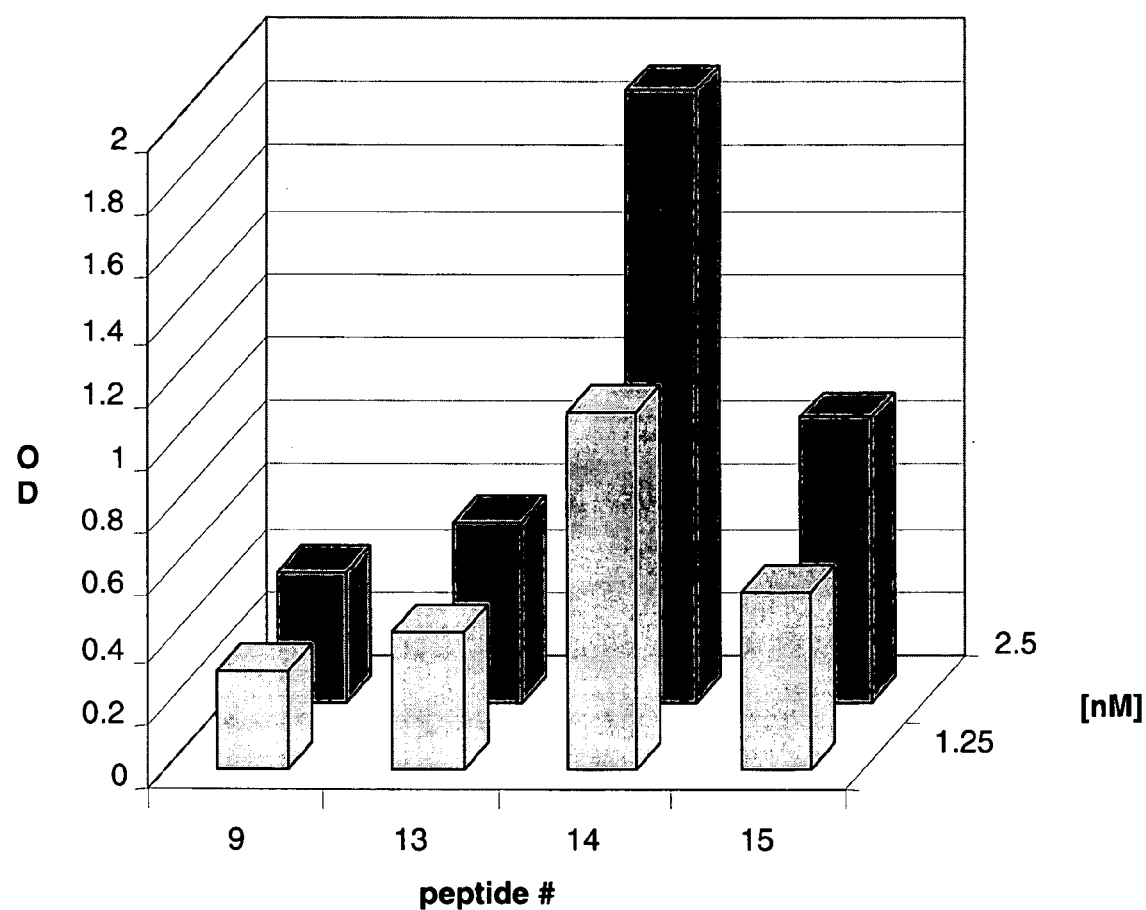
FIG. 12 shows the effects of a nuclear localization signal on PTD transport.

The results are shown in FIG. 12. The presence of a localization signal did not adversely effect translocation of the complex. A nuclear localization signal located on the carboxy terminus of the PTD (SEQ ID NO:19) functioned much better in translocating the complex than nuclear localization signals located on the amino terminus of the PTD.

Figure 13:
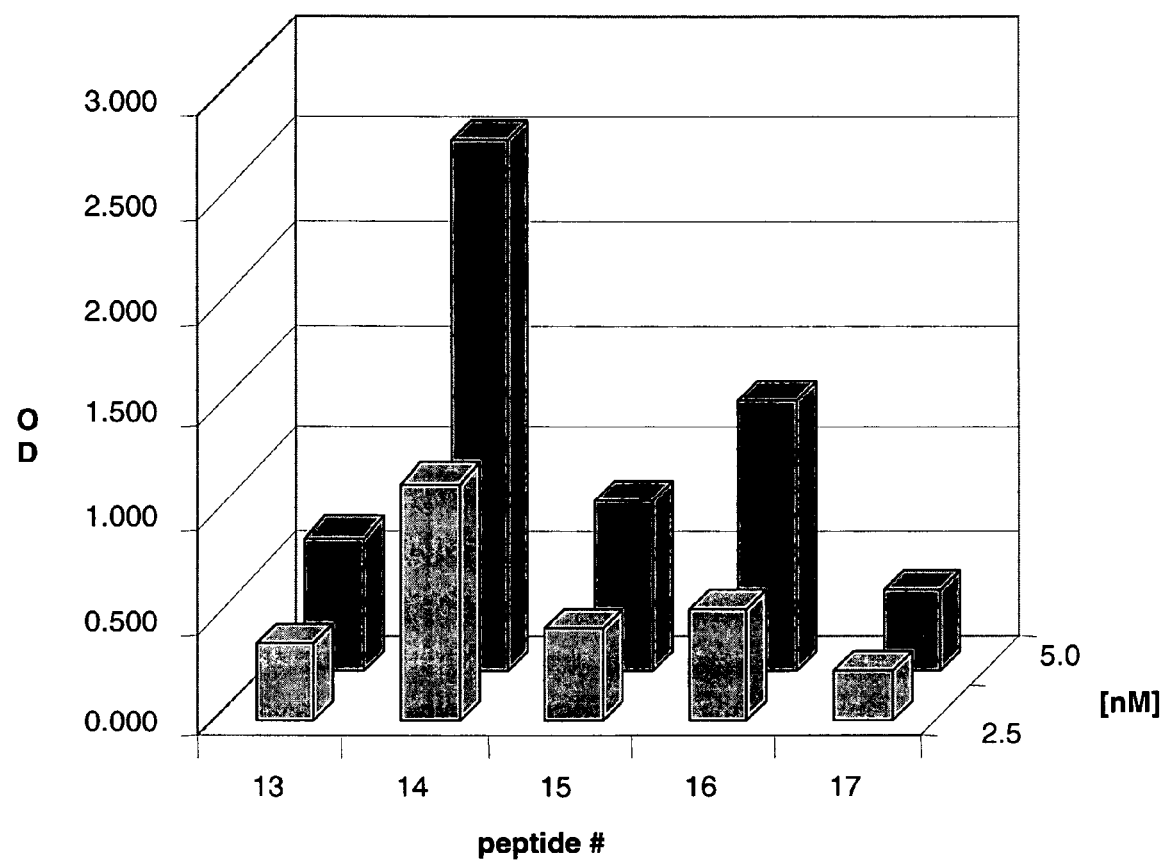
FIG. 13 shows the effects of multiple nuclear localization signals on PTD transport and the position effects of the nuclear localization signal around an N-terminal lysine linker.

Peptides containing two nuclear localization signals were tested to study the role of the multiple nuclear localization signals on peptide transport. The amino acid sequences of the peptides are listed in Table 3. NIH 3T3 cells were seeded as described above. A PTD-β-galactosidase complex was added to a final concentration of 20 nM, and the cells were incubated for 1 hour at 37° C. Following incubation, the cells were washed 3 times in PBS and assayed for nuclear localization of β-galactosidase. The results are shown in FIG. 13. Multiple nuclear localization signals did not enhance transport into the cells.

TABLE 3

| | |
|---|---|
| Biotin-Lys-Gly-Gly-Arg-Lys-Met-Leu-Lys-Ser-Thr-Arg-Arg-Gln-Arg-Arg (Biotin-Lys-InvRP5 or peptide 9) | (SEQ ID NO:14) |
| Biotin-Lys-Gly-Gly-Lys-Lys-Lys-Arg-Lys-Val-Met-Leu-Lys-Ser-Thr-Arg-Arg-Gln-Arg-Arg (peptide 13) | (SEQ ID NO:18) |
| Biotin-Lys-Gly-Gly-Arg-Lys-Met-Leu- | (SEQ ID NO:19) |

TABLE 3-continued

Lys-Ser-Thr-Arg-Arg-Gln-Arg-Arg-Lys-Lys-Lys-Arg-Lys-Val (peptide 14)

Biotin-Lys-Lys-Lys-Arg-Lys-Val-Lys-Gly-Gly-Arg-Lys-Met-Leu-Lys-Ser-Thr-Arg-Arg-Gln-Arg-Arg (peptide 15) (SEQ ID NO:20)

Biotin-Lys-Gly-Gly-Arg-Lys-Met-Leu- (SEQ ID NO:21)

Lys-Ser-Thr-Arg-Arg-Gln-Arg-Arg-Lys-Lys-Lys-Arg-Lys-Val (peptide 16)

Biotin-Lys-Lys-Lys-Arg-Lys-Val-Lys-Gly-Gly-Lys-Lys-Lys-Arg-Val-Met-Leu-Lys-Ser-Thr-Arg-Arg-Gln-Arg-Arg (peptide 17) (SEQ ID NO:22)

---

I claim:

1. An isolated and purified polypeptide with a protein transduction domain (PTD) which comprises Arg-Lys-Met-Leu-Lys-Ser-Thr-Arg-Arg-Gln-Arg-Arg (SEQ ID NO:1), wherein the polypeptide can traverse a cellular membrane.

2. The polypeptide of claim 1 further comprising at its amino terminus Lys-Xaa-Xaa, wherein Xaa is a small neutral polar or nonpolar amino acid.

3. The polypeptide of claim 2 comprising the amino acid sequence Lys-Gly-Gly-Arg-Lys-Met-Leu-Lys-Ser-Thr-Arg-Arg-Gln-Arg-Arg (SEQ ID NO:2).

4. The polypeptide of claim 1 further comprising a chemical cross-linker.

5. The polypeptide of claim 4 wherein the chemical cross-linker is maleimide or 3-nitro-2-pyridyldithio group.

6. A complex comprising a cargo moiety complexed with a polypeptide comprising a protein transduction domain (PTD) wherein said polypeptide is capable of complexing with said cargo moiety and wherein the PTD comprises Arg-Lys-Met-Leu-Lys-Ser-Thr-Arg-Arg-Gln-Arg-Arg (SEQ ID NO:1), and wherein the complex can traverse a cellular membrane.

7. The complex of claim 6 wherein the cargo moiety is selected from the group consisting of a small molecule, a nucleic acid, and a polypeptide.

8. The complex of claim 7 wherein the cargo moiety is a small molecule, wherein the small molecule is selected from the group consisting of a fluorescent marker, a dye, and a pharmaceutical agent.

9. The complex of claim 6 wherein said polypeptide comprising said PTD is a fusion protein.

10. The complex of claim 7 wherein the cargo moiety is a small molecule, wherein the small molecule comprises a radionuclide.

11. The complex of claim 6 wherein the cargo moiety is β-galactosidase or alkaline phosphatase.

12. A conjugate comprising a polypeptide with a protein transduction domain (PTD) linked to a cargo moiety, wherein the PTD comprises Arg-Lys-Met-Leu-Lys-Ser-Thr-Arg-Arg-Gln-Arg-Arg (SEQ ID NO:1), and wherein the conjugate can traverse a cellular membrane.

13. The conjugate of claim 12, wherein the cargo moiety is selected from the group consisting of a small molecule, a nucleic acid, and a polypeptide.

14. The conjugate of claim 12, wherein the conjugate comprises a fusion protein.

15. The conjugate of claim 12, wherein the cargo moiety is β-galactosidase or alkaline phosphatase.

* * * * *

(12) EX PARTE REEXAMINATION CERTIFICATE (8556th)
United States Patent
Karas

(10) Number: US 7,166,692 C1
(45) Certificate Issued: Sep. 20, 2011

(54) INTRACELLULAR DELIVERY OF SMALL MOLECULES, PROTEINS AND NUCLEIC ACIDS

(75) Inventor: Michael Karas, Rockville, MD (US)

(73) Assignee: Lonza Walkersville Inc., Walkersville, MD (US)

Reexamination Request:
No. 90/011,324, Nov. 10, 2010

Reexamination Certificate for:
Patent No.: 7,166,692
Issued: Jan. 23, 2007
Appl. No.: 10/790,768
Filed: Mar. 3, 2004

Related U.S. Application Data

(60) Provisional application No. 60/451,243, filed on Mar. 4, 2003.

(51) Int. Cl.
*C07K 7/00* (2006.01)

(52) U.S. Cl. ....................................... 530/300
(58) Field of Classification Search .................... 530/300
See application file for complete search history.

(56) References Cited

U.S. PATENT DOCUMENTS 5,128,319 A    7/1992   Arlinghaus et al.

6,316,003 B1    11/2001   Frankel et al.

FOREIGN PATENT DOCUMENTS

WO    WO 01/15511 A2    3/2001

OTHER PUBLICATIONS

Mi, Z., et al., "Characterization of a Class of Cationic Peptides Able to Facilitate Efficient Protein Transduction in Vitro and in Vivo," *Mol. Ther.* 2:339–347, The American Society of Gene Therapy (2000).

Wender, P., et al., "The design, synthesis, and evaluation of molecules that enable or enhance cellular uptake: Peptoid molecular transporters," *Proc. Natl. Acad. Sci. U.S.A.* 97:13003–13008, National Academy of Sciences (2000).

DeRossi, D., et al., "Cell Internalization of the Third Helix of the Antennapedia Homeodomain Is Receptor–independent," *J. Biol.Chem.* 271:18188–18193, The American Society for Biochemistry and Molecular Biology, Inc. (1996).

*Primary Examiner*—Johnny F Railey

(57) ABSTRACT

An amino acid sequence Arg-Lys-Met-Leu-Lys-Ser-Thr-Arg-Arg-Gln-Arg-Arg (SEQ ID NO:1) functions as a protein transduction domain (PTD) and is capable of delivering small molecules, proteins, and nucleic acids to an intracellular compartment of a cell. An amino terminal lysine linker improves the efficiency of the PTD. A nuclear localization signal can be used to target the PTD to a cell's nucleus. The PTD can be used in PTD-cargo moiety complexes that can reversibly immortalize cells and increase cell viability in culture.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-15 are cancelled.

* * * * *